(12) United States Patent
Smits

(10) Patent No.: US 6,741,893 B2
(45) Date of Patent: May 25, 2004

(54) MEDICAL ELECTRICAL LEAD HAVING VARIABLE BENDING STIFFNESS

(75) Inventor: Karel F. A. Smits, Munstergeleen (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/947,065

(22) Filed: Sep. 6, 2001

(65) Prior Publication Data

US 2002/0065544 A1 May 30, 2002

Related U.S. Application Data

(62) Division of application No. 09/449,934, filed on Nov. 29, 1999.

(51) Int. Cl.$^7$ ................................. A61N 1/05
(52) U.S. Cl. .................................... 607/122
(58) Field of Search ................ 600/372–375, 600/377, 381; 607/115–116, 119, 122–123, 125–131

(56) References Cited

U.S. PATENT DOCUMENTS

| | | | |
|---|---|---|---|
| 3,825,015 A | 7/1974 | Berkovits | 128/404 |
| 3,865,118 A | 2/1975 | Bures | 128/404 |
| 3,903,897 A | 9/1975 | Woollons et al. | 128/419 PG |
| 3,911,928 A | 10/1975 | Lagergren | 128/418 |
| 3,935,864 A | 2/1976 | Lagergren | 128/418 |
| 3,949,757 A | 4/1976 | Sabel | 128/404 |
| 4,057,067 A | 11/1977 | Lajos | 128/418 |
| 4,154,247 A | 5/1979 | O'Neill | 128/419 P |
| 4,215,703 A | 8/1980 | Willson | 128/772 |
| 4,289,144 A | 9/1981 | Gilman | 128/785 |
| 4,328,812 A | 5/1982 | Ufford et al. | 128/786 |
| 4,393,883 A | 7/1983 | Smyth et al. | 128/785 |
| 4,401,126 A | 8/1983 | Reenstierna | 178/784 |

(List continued on next page.)

OTHER PUBLICATIONS

"Orthogonal Electrogram Sensing", B.N. Goldreyer et al., PACE, vol. 6, Mar.–Apr. 1983, Part II, pp. 464–469.

"Sensing Characteristics of Unipolar and Bipolar Orthogonal Floating Atrial Electrodes: Morphology and Spectral Analysis", A.E. Aubert, et al., PACE, vol. 9, May–Jun. 1986, pp. 343–359.

"Toward Optimizing the Detection of Atrial Depolarization with Floating Bipolar Electrodes", R.R. Brownlee, PACE, vol. 12, Mar. 1989, pp. 431–442.

"Amplitude and Direction of Atrial Depolarization Using a Multipolar Floating Catheter: Principles for a Single Lead VDD Pacing", D. Flammang, et al., PACE, vol. 14, Jun. 1991, pp. 1040–1048.

(List continued on next page.)

Primary Examiner—Kennedy Schaetzle
Assistant Examiner—Kristen Droesch
(74) Attorney, Agent, or Firm—Girma Wolde-Michael

(57) ABSTRACT

An elongated coronary vein lead having a variable stiffness lead body and most preferably adapted to be advanced into a selected coronary vein for delivering a pacing or defibrillation signal to a predetermined region of a patient's heart, such as the left ventricle is disclosed. A method of pacing and/or defibrillating a patient's heart using the lead is also described. The method of pacing or defibrillating the heart includes advancing the coronary vein lead through both the coronary sinus and into a selected coronary vein of a patient's heart, connecting the lead to an electrical pacing source and applying electrical stimulation to a particular chamber of the patient's heart via the implanted lead. The lead includes a variable stiffness lead body that enhances the ability of the lead to be retained in a coronary vein after the lead has been implanted therein.

4 Claims, 24 Drawing Sheets

U.S. PATENT DOCUMENTS

| | | | | |
|---|---|---|---|---|
| 4,401,127 A | | 8/1983 | Littleford | 128/786 |
| 4,402,328 A | | 9/1983 | Doring | 128/785 |
| 4,402,330 A | | 9/1983 | Lindemans | 128/786 |
| 4,422,460 A | | 12/1983 | Pohndorf | 128/786 |
| 4,444,195 A | | 4/1984 | Gold | 128/642 |
| 4,458,677 A | | 7/1984 | McCorkle, Jr. | 128/786 |
| 4,493,329 A | | 1/1985 | Crawford et al. | 128/786 |
| 4,502,492 A | | 3/1985 | Bornzin | 128/785 |
| 4,567,901 A | | 2/1986 | Harris | 128/786 |
| 4,627,439 A | | 12/1986 | Harris | 128/419 P |
| 4,727,877 A | | 3/1988 | Kallok | 128/419 D |
| 4,882,777 A | | 11/1989 | Narula | 604/281 |
| 4,913,147 A | | 4/1990 | Fahlstrom et al. | 128/419 P |
| 4,930,521 A | | 6/1990 | Metzger et al. | 128/786 |
| 4,962,767 A | | 10/1990 | Brownlee | 128/786 |
| 5,111,811 A | | 5/1992 | Smits | 128/419 D |
| 5,133,422 A | | 7/1992 | Coury et al. | 128/784 |
| 5,144,960 A | | 9/1992 | Mehra et al. | 128/786 |
| 5,172,694 A | | 12/1992 | Flammang et al. | 128/642 |
| 5,273,053 A | | 12/1993 | Pohndorf | 607/132 |
| 5,306,263 A | | 4/1994 | Voda | 604/281 |
| 5,308,342 A | | 5/1994 | Sepetka et al. | 604/282 |
| 5,330,521 A | | 7/1994 | Cohen | 607/122 |
| 5,423,772 A | | 6/1995 | Lurie et al. | 604/282 |
| 5,437,632 A | | 8/1995 | Engelson | 604/53 |
| 5,476,497 A | * | 12/1995 | Mower et al. | 607/122 |
| 5,499,973 A | | 3/1996 | Saab | 604/96 |
| 5,531,685 A | | 7/1996 | Hemmer et al. | 604/95 |
| 5,605,162 A | | 2/1997 | Mirzaee et al. | 128/772 |
| 5,628,778 A | | 5/1997 | Kruse et al. | 607/123 |
| 5,639,276 A | | 6/1997 | Weinstock et al. | 606/129 |
| 5,683,445 A | * | 11/1997 | Swoyer | 607/125 |
| 5,733,496 A | | 3/1998 | Avellanet | 264/470 |
| 5,749,849 A | | 5/1998 | Engelson | 604/53 |
| 5,755,765 A | | 5/1998 | Hyde et al. | 607/122 |
| 5,755,766 A | | 5/1998 | Chastain et al. | 607/122 |
| 5,803,928 A | | 9/1998 | Tockman et al. | 607/122 |
| 5,810,867 A | | 9/1998 | Zarbatany et al. | 606/191 |
| 5,833,604 A | | 11/1998 | Houser et al. | 600/373 |
| 5,855,560 A | | 1/1999 | Idaomi et al. | 600/585 |
| 5,871,531 A | | 2/1999 | Struble | 607/126 |
| 5,897,584 A | | 4/1999 | Herman | 607/122 |
| 5,925,073 A | | 7/1999 | Chastain et al. | 607/122 |
| 5,931,819 A | | 8/1999 | Fariabi | 604/281 |
| 5,931,864 A | | 8/1999 | Chastain et al. | 607/128 |
| 5,935,160 A | | 8/1999 | Auricchio et al. | 607/122 |
| 5,951,597 A | | 9/1999 | Westlund et al. | 607/126 |
| 6,006,139 A | * | 12/1999 | Kruse et al. | 607/125 |
| 6,148,238 A | * | 11/2000 | Rutten | 607/126 |
| 6,400,992 B1 | * | 6/2002 | Borgersen et al. | 607/122 |

OTHER PUBLICATIONS

"Permanent Pervenous Atrial Sensing and Pacing with a New J–shaped Lead", Smyth et al., Journ. Of Thoracic and Cardiovascular Surgery, 1976, No. 72, pp. 565–570.

"18 Months of Clinical Experience with the Implantable Optimized Sequential Stimulator", H.D. Funke, World Symposium on Cardiac Pacing, $6^{th}$, Montreal, Quebec, 1979: Montreal PaceSymp., 1979, Chapter 16–3.

"A New Lead for Transvenous Atrial Pacing and Sensing", Kruse et al., PACE, Jul.–Aug. 1980, vol. 3, pp. 395–405.

"Three Year Clinical Experience with a New Endocardial Screw–in Lead with Introduction Protection for Use in the Atrium and Ventricle", Bisping et al., PACE, Jul.–Aug. 1980, vol. 3, pp. 424–435.

"Crown of Thorns'–Single Pass Lead–Clinical Results", Sowton et al., PACE, Mar.–Apr. 1983, Part II, vol. 6, pp. 470–474.

"Sensing and Pacing with Floating Electrodes in the Right Atrium and Right Atrial Appendage", Aubert et al., Journ. Of Amer. College of Cardiology, 1987, Col. 9, No. 2, pp. 308–315.

"European Multicenter Prospective Follow–Up Study of 1,002 Implants of a Single Lead VDD Pacing System", J.C. Pitts Crick, PACE, 1991, vol. 14, pp. 1742–1744.

"Medtronic Model 2188 Endocardial, Bipolar, Coronary Sinus Pacing Lead: Technical Manual".

\* cited by examiner

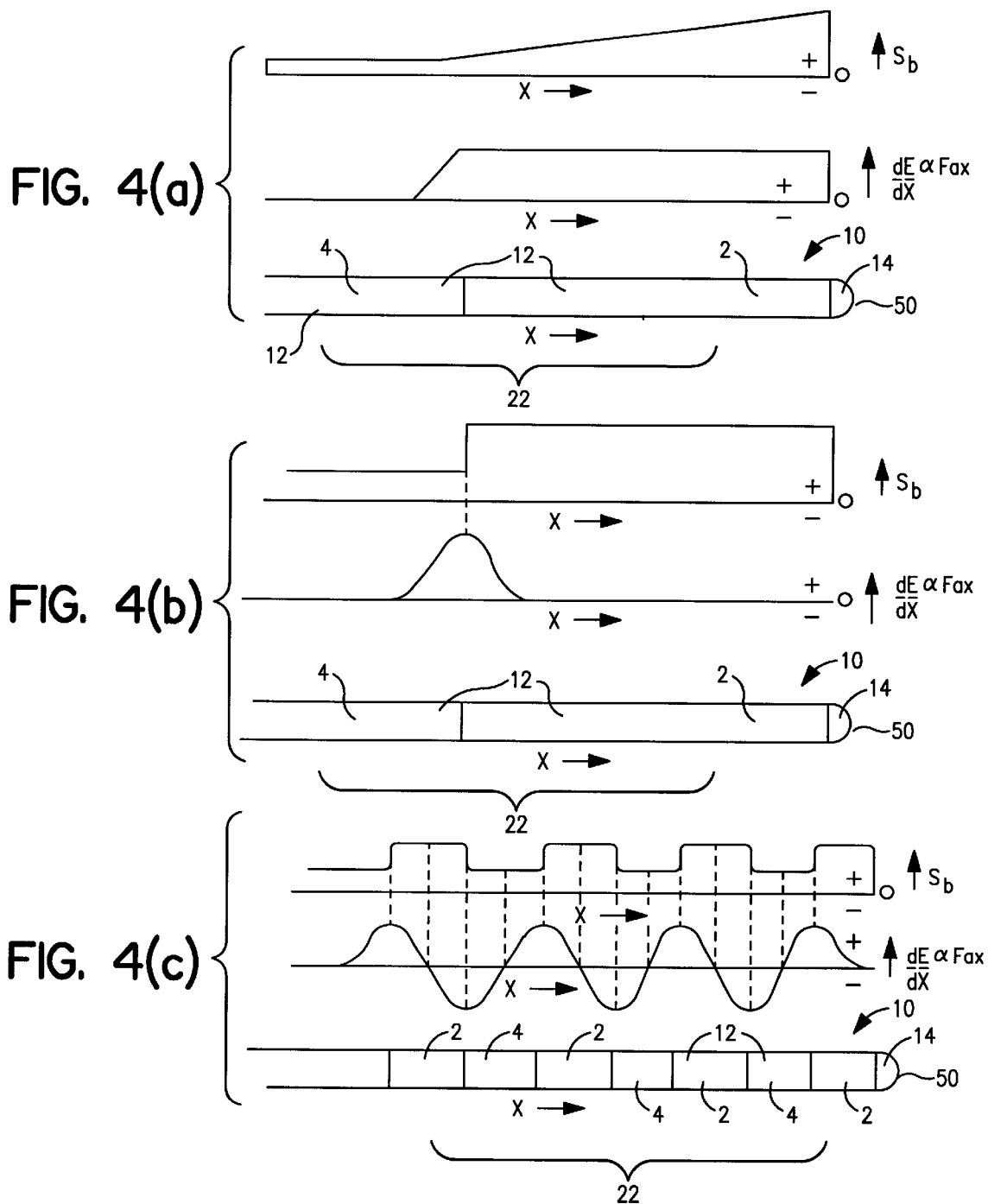

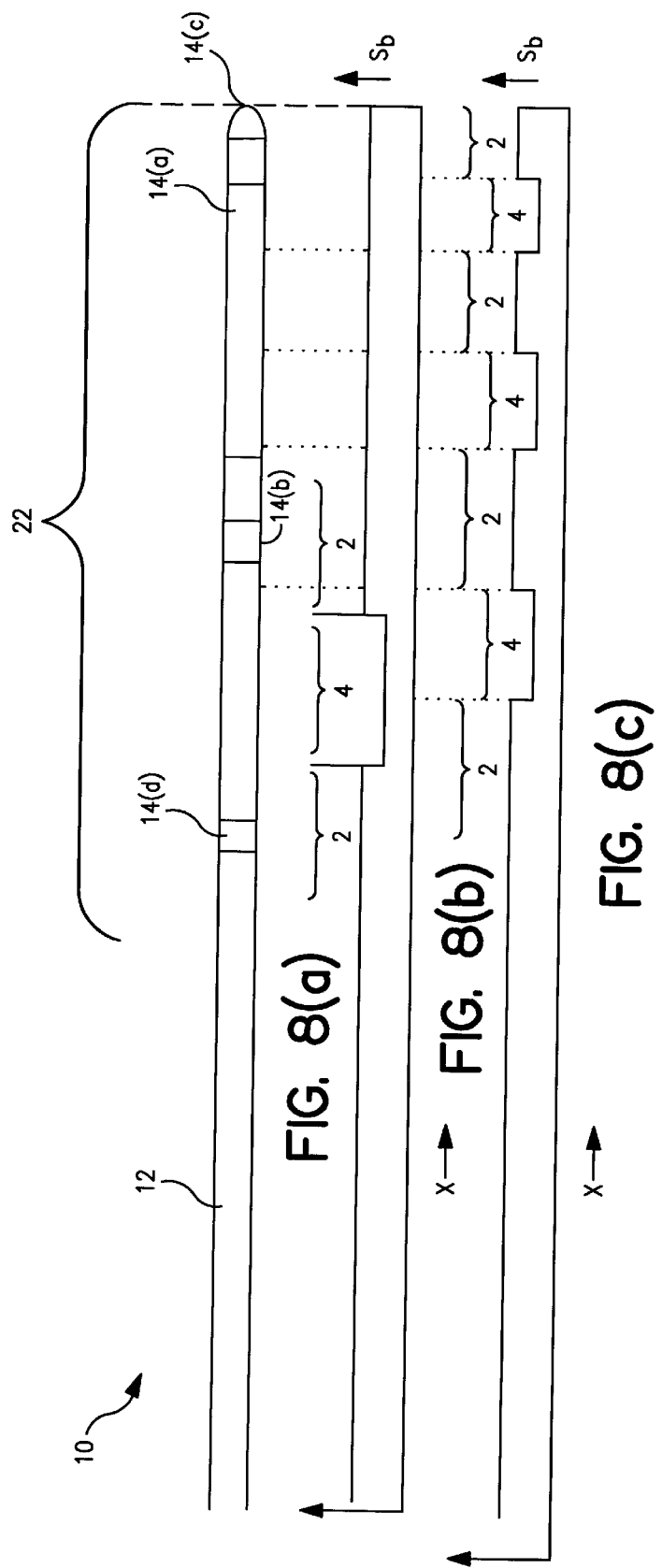

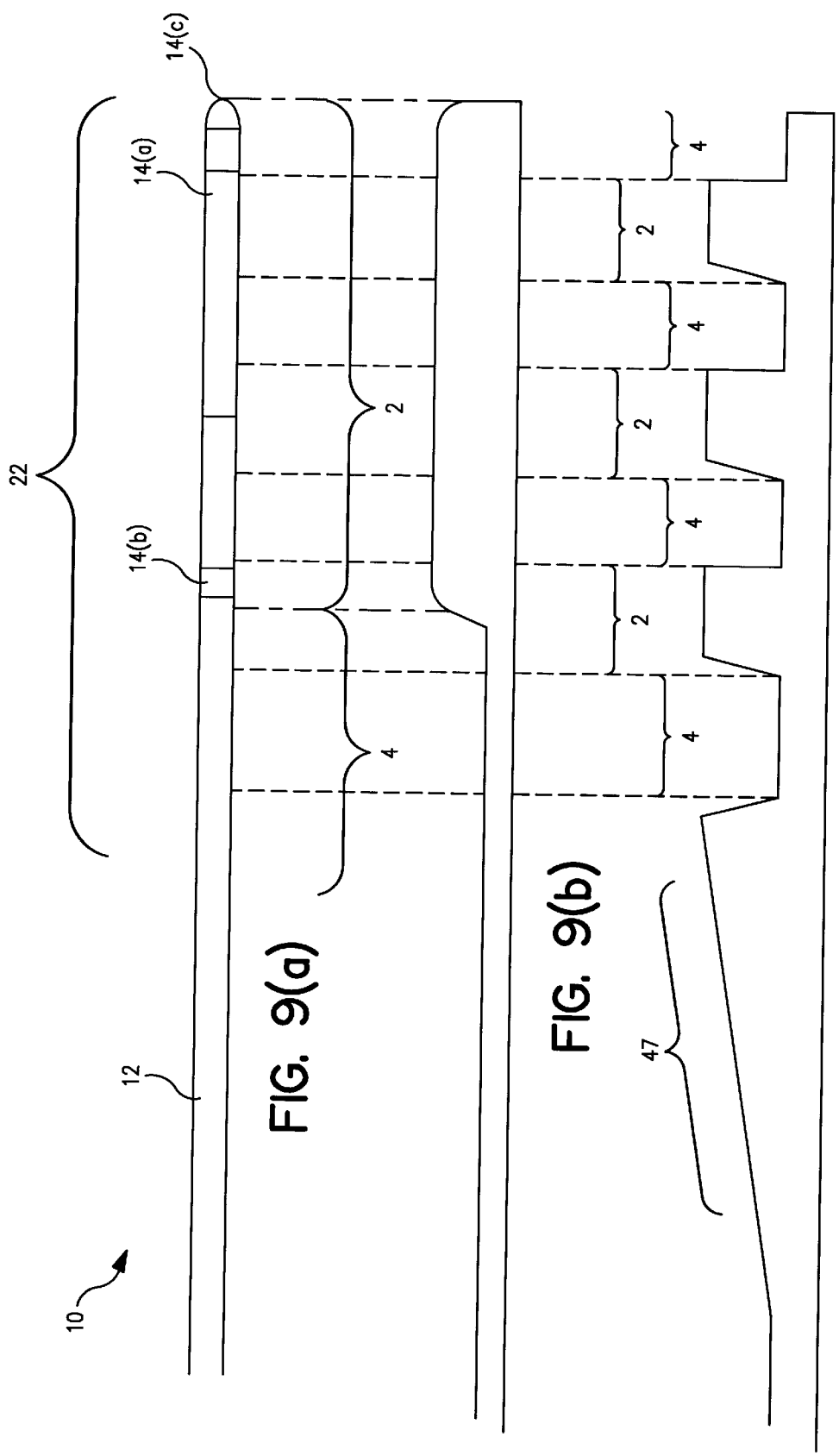

(Constant Pitch Coils)

(Constant-Diameter, Variable-Pitch Coils)

MEDICAL ELECTRICAL LEAD HAVING VARIABLE BENDING STIFFNESS

This is a division of Ser. No. 09/449,934, filed Nov. 29, 1999. This patent application hereby incorporates by reference herein, in its entirety, U.S. patent application Ser. No. 09/449,936, filed Nov. 29, 1999 for "Medical Electrical Lead Having Bending Stiffnesses Which Increase In The Distal Direction" to Smits now U.S. Pat. No. 6,549,812.

FIELD OF THE INVENTION

The present invention relates to pacing and defibrillation medical electrical leads. The present invention also relates to such leads adapted and configured for implantation within the coronary sinus and coronary veins.

BACKGROUND OF THE INVENTION

Transvenously inserted leads for implantable cardiac pacemakers have conventionally been positioned within the right atrium or right ventricle of the patient's heart for pacing or defibrillating the right atrium and/or right ventricle, respectively. While it is relatively safe to insert a pacing or defibrillation lead and its associated electrodes into the right atrium or right ventricle, there is a reluctance to install a similar lead in the left ventricle because of the possibility of clot formation and resulting stroke.

When a lead is implanted within a patient's circulatory system, there is always the possibility of a thrombus being generated and released. If the lead is positioned in the right atrium or right ventricle, a generated thrombus tends to migrate through the pulmonary artery and is filtered by the patient's lungs. A thrombus generated in the left atrium or left ventricle, however, would pose a danger to the patient due to the possibility of a resulting ischemic episode.

Thus, in those instances where left heart stimulation is desired, it has been a common practice to use an intercostal approach using a myocardial screw-in, positive-fixation lead. The screw-in lead may, however, be traumatic for the patient. There are additional instances when left ventricular pacing is desired, such as during bi-ventricular pacing. In U.S. Pat. No. 4,928,688, Mower describes an arrangement for achieving bi-ventricular pacing in which electrical stimulating pulses are applied via electrodes disposed on a single pacing lead to both the right and left ventricular chambers so as to obtain a coordinated contraction and pumping action of the heart. The '688 patent also discloses a split pacing lead having first and second separate electrodes, wherein the first electrode is preferably introduced through the superior vena cava for pacing the right ventricle and the second electrode is introduced through the coronary sinus for pacing the left ventricle. Other electrode leads which are inserted into the coronary sinus have been described. For example, in U.S. Pat. No. 5,014,696 to Mehra and U.S. Pat. No. 4,932,407 to Williams endocardial defibrillation electrode systems are disclosed.

Still other leads and catheters have been proposed, including those described in the patents listed in Table 1 below.

TABLE 1

| U.S. Pat. No. | Title |
|---|---|
| 5,951,597 | Coronary sinus lead having expandable matrix anchor |
| 5,935,160 | Left ventricular access lead for heart failure pacing |
| 5,931,864 | Coronary venous lead having fixation mechanism |
| 5,931,819 | Guidewire with a variable stiffness distal portion |
| 5,925,073 | Intravenous cardiac lead with wave shaped fixation segment |
| 5,897,584 | Torque transfer device for temporary transvenous endocardial lead |
| 5,871,531 | Medical electrical lead having tapered spiral fixation |
| 5,855,560 | Catheter tip assembly |
| 5,833,604 | Variable stiffness electrophysiology catheter |
| 5,810,867 | Dilation catheter with varied stiffness |
| 5,803,928 | Side access "over the wire" pacing lead |
| 5,755,766 | Open-ended intravenous cardiac lead |
| 5,755,765 | Pacing lead having detachable positioning member |
| 5,749,849 | Variable stiffness balloon catheter |
| 5,733,496 | Electron beam irradiation of catheters to enhance stiffness |
| 5,639,276 | Device for use in right ventricular placement and method for using same |
| 5,628,778 | Single pass medical electrical lead |
| 5,605,162 | Method for using a variable stiffness guidewire |
| 5,531,685 | Steerable variable stiffness device |
| 5,499,973 | Variable stiffness balloon dilatation catheters |
| 5,437,632 | Variable stiffness balloon catheter |
| 5,423,772 | Coronary sinus catheter |
| 5,330,521 | Low resistance implantable electrical leads |
| 5,308,342 | Variable stiffness catheter |
| 5,144,960 | Transvenous defibrillator lead and method of use |
| 5,111,811 | Cardioversion and defibrillation lead system with electrode extension into the Coronary sinus and great vein |
| 4,930,521 | Variable stiffness esophageal catheter |
| 4,215,703 | Variable stiffness guide wire |
| 08/794,175 | Single Pass Medical Electrical Lead |
| 08/794,402 | Single Pass Medical Electrical Lead with Cap Electrodes |

As those skilled in the art will appreciate after having reviewed the specification and drawings hereof, at least some of the devices and methods discussed in the patents of Table 1 may be modified advantageously in accordance with the present invention. All patents listed in Table 1 herein above are hereby incorporated by reference herein, each in its respective entirety.

Prior art coronary vein leads for heart failure applications (i.e., pacing leads) or sudden death applications (i.e., defibrillation leads) generally must be wedged in a coronary vein to obtain a stable mechanical position and to prevent dislodgment. While such an arrangement is generally acceptable for defibrillation leads (which usually must be implanted with the distal tip thereof located near the apex of the heart), such is not the case for heart failure or pacing leads, where more basal stimulation of the heart is generally desired. Basal stimulation of the heart via the coronary vein, however, presents certain difficulties because vein diameters in the basal area of the heart are large and generally do not permit the distal end or tip of a pacing lead to be sufficiently well wedged therein.

Thus, there exits a need to provide a pacing or defibrillation medical electrical lead which is capable of being implanted within both larger diameter and smaller diameter portions of the coronary vein anatomy of a human heart where the lead does not require lead tip wedging. There is also a need to provide a medical electrical lead for pacing and defibrillation applications in which the orientation of an electrode mounted on a distal portion thereof may be controlled and adjusted to permit the electrode to point towards the left ventricular myocardium or other selected portions of the heart accessible via the coronary vein anatomy to thereby minimize pacing thresholds and improve sensing. There is a further need to provide a medical electrical lead for pacing and defibrillation applications in which the orientation of a pacing or defibrillation electrode disposed on a distal portion thereof may be determined using conventional x-ray or echo/acoustic techniques.

SUMMARY OF THE INVENTION

The present invention has certain objects. That is, the present invention provides solutions to one or more problems existing in the prior art. For example, various embodiments of the present invention have one or more of the following objects: (a) providing a medical electrical lead suitable for implantation in the coronary sinus or coronary vein which is not pushed out of the coronary sinus or coronary vein once implanted therein; (b) providing a medical electrical lead suitable for implantation within relatively large diameter portions of the coronary sinus and coronary vein without requiring wedging or the use of positive fixation means such as tines, helical screws or the like; (c) providing a medical electrical lead which exhibits enhanced removability following implantation and fibrosis; and (d) providing a medical electrical lead suitable for implantation within the coronary sinus or coronary veins which requires less time and effort to implant.

Various embodiments of the present invention suitable for implantation within the coronary sinus or coronary veins possess certain advantages, including one or more of the following: (a) exhibiting multiple lead mechanical stability points which are not dependent on any positive fixation mechanisms such as wedging, hooking, screwing or clamping; (b) providing a lead whose retention within the coronary veins is less dependent upon the particular shape or diameter of such veins than prior art leads; (c) providing a lead which permits improved pacing electrode positioning within the coronary venous anatomy; (d) providing a lead which permits lower pacing thresholds and improved sensing of intra-cardiac signals; (e) providing a lead which permits the one or more electrodes thereof to be oriented towards the myocardium or other selected portions of the heart; (f) providing a lead which exhibits improved acute and chronic pacing thresholds and sensing characteristics; (g) providing a lead which has no or reduced positive fixation mechanisms attached thereto; (h) providing a lead which may be implanted with an introducer of reduced size; (i) providing a lead which improves chronic lead removability thereof; (j) providing a straight lead which is easier, more reproducible and less expensive to manufacture; (k) providing a single pass medical electrical lead for dual chamber pacing of the left atrium and left ventricle via implantation within the coronary sinus and great cardiac vein; and (l) providing a medical electrical lead having a stiffness which varies as a function of axial distance adapted for specific placement and stability within veins other than the coronary sinus and great cardiac veins, wherein the lead exhibits appropriate distal curvature and stiffness required for implantation within the hepatic vein, spinal column, sub-cutaneously, or in other locations within the human body.

Various embodiments of the present invention exhibit one or more of the following features: (a) a distal section of a pacing or defibrillation lead having variable bending stiffness adapted and configured to create a forward driving force of the lead when the variable bending stiffness portion of the distal end of the lead is subjected to a sufficient bending moment; (b) a pacing or defibrillation lead having in a distal portion thereof a variable bending stiffness section in which the bending stiffness increases with respect to axial distance; (c) a medical electrical lead which owing to variations in bending stiffness along its axial direction imparts a positive tip force or a forward driving force to the lead, and where bending of the lead may preferentially take place along different pre-determined bending planes (e.g., three dimensional bending along multiple preferred orientations); (d) a pacing or defibrillation lead wherein variations in bending stiffness are rotationally symmetric; (e) a pacing or defibrillation lead wherein bending stiffness is rotationally asymmetric to permit orientation of one or more electrodes, fixation means, or other lead features relative to the bending plane of a bent or curved section; (f) a pacing or defibrillation lead exhibiting variable stiffness over at least distal portions thereof and which further comprises one or more of active or passive fixation features, a unipolar or multi-polar configuration, is a pacing or sensing lead, is a defibrillation lead, and/or has a combination of pacing/sensing and/or defibrillation capabilities. Methods of making, using, and implanting a lead of the present invention are also contemplated in the present invention.

These and other objects, features and advantages of the present invention will become readily apparent to those skilled in the art from a review of the following detailed description of the preferred embodiments in conjunction with the accompanying drawings, in which like numerals in the several views refer to corresponding parts.

BRIEF DESCRIPTION OF THE DRAWINGS

FIGS. 4A–4C illustrate schematically several different embodiments of leads of the present invention and their corresponding bending stiffnesses and derivatives of stored mechanical energy with respect to axial distance;

FIGS. 8A–9C illustrate two different embodiments of the distal sections of lead bodies of the present invention and corresponding bending stiffness profiles as a function of axial distance;

DETAILED DESCRIPTION OF THE PREFERRED EMBODIMENT

Figure 1:
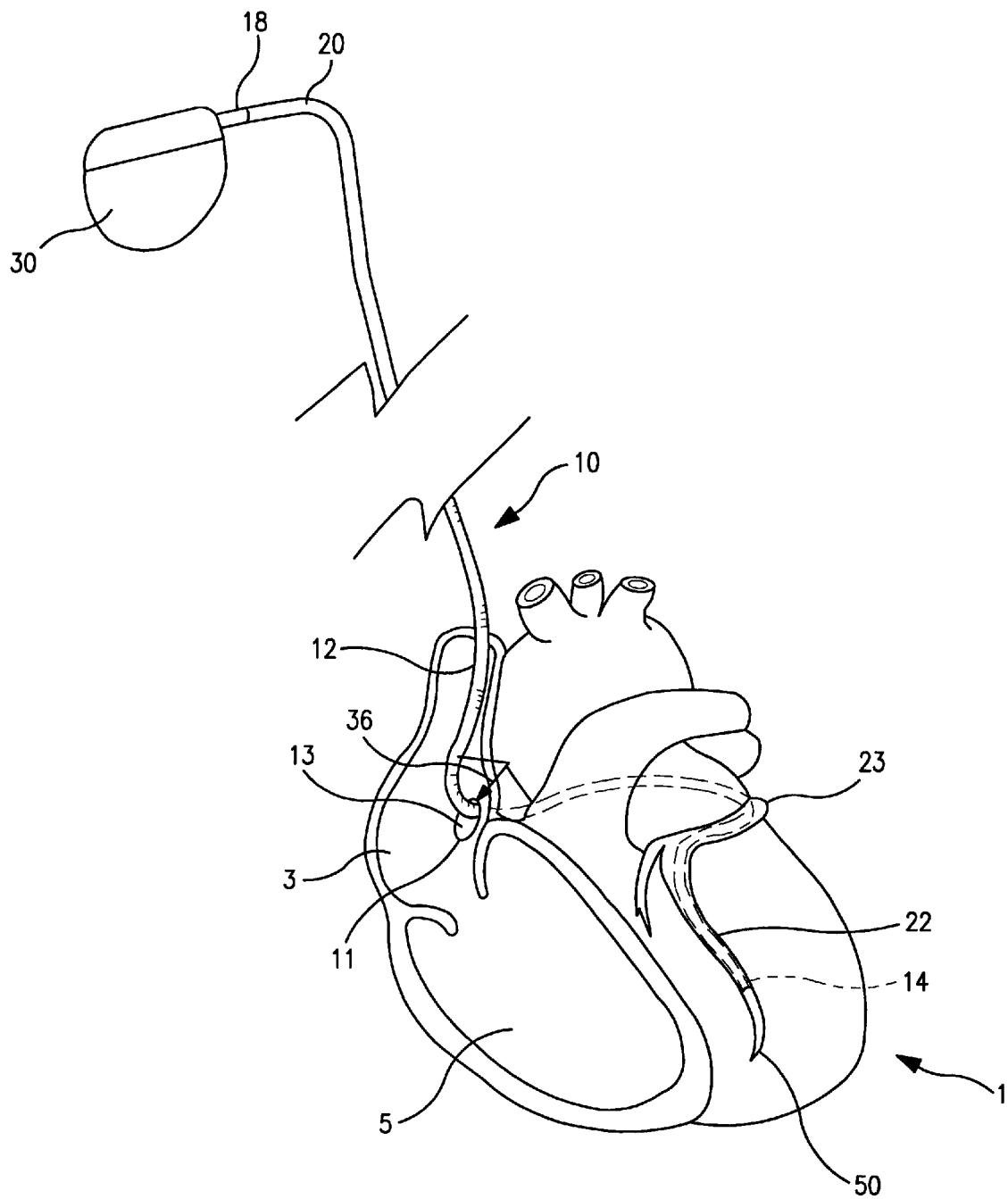
FIG. 1 shows a partial cross-sectional view of a human heart with one embodiment of a lead of the present invention in combination with a cardiac stimulator.

FIG. 1 shows human heart 1 with medical electrical lead 10 of the present invention implanted therein. Proximal end 20 of medical electrical lead 10 is connected to implantable cardiac stimulator 30 by means of connector or terminal 18. Cardiac stimulator 30 may be a pacemaker, an implantable pulse generator (IPG), an implantable cardiodefibrillator (ICD), a pacer-cardioverter-defibrillator (PCD), or any other type of similar cardiac stimulator well known in the art. Medical electrical lead 10 comprises proximal portion 20, distal portion 22 and lead body 12. Tip 50 is disposed at the distalmost end of lead 10. As shown in FIG. 1, lead 10 enters right atrium 3 and then winds its way through ostium 11 into coronary sinus 13 and then through great cardiac vein 23 to the distalmost portion thereof. Medical electrical lead 10 comprises one or more electrodes 14 disposed thereon for pacing, sensing and/or defibrillating heart 1.

Figure 2:
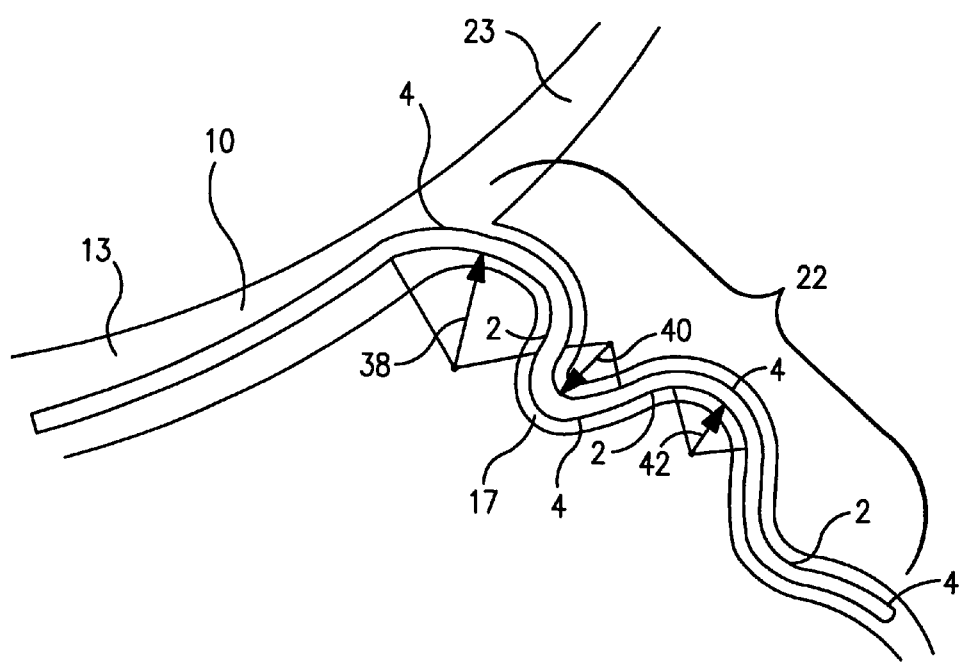
FIG. 2 shows a partial cross-sectional view of a heart having one embodiment of a lead of the present invention disclosed therein.

Referring now to FIG. 2, there is shown a cross-sectional view of lead 10 disposed in, for example, posterior cardiac vein 17 of heart 1 via coronary sinus 13 and great cardiac vein 23. At least portions of distal portion 22 of lead 10 are located in posterior cardiac vein 17. FIG. 2 illustrates how lead 10 must be routed through a series of winding tortuous pathways when implanted in the cardiac veins. Such pathways not only make implantation and placement of lead 10 in desired portions of heart 1 difficult, but also have a tendency to cause prior art leads to be pushed out of the cardiac vein in which they are located once implanted, further discussion concerning which follows below.

Continuing to refer to FIG. 2, there is shown medical electrical lead 10 of the present invention which prior to implantation most preferably has a straight distal section 22 adapted for implantation within coronary sinus 13, great cardiac vein 23, or within any other of the left ventricular coronary veins or left atrial veins when appropriately configured and dimensioned. In the present invention, the bending stiffness of distal section 22 of lead 10 is made variable so as to increase or decrease in a predetermined singular or periodic fashion.

Thus, in one embodiment of the present invention distal portion 22 of lead 10 has at least one distalmost stiff section 2 disposed distally of a flexible section 4 located adjacent thereto. That is, lead body 12 may be configured to have at least one stiff section 2 and at least one flexible section 4 located in distal portion 22 thereof. Medical electrical lead 10 of the present invention may additionally have adjacent adjoining portions which alternate between being flexible and being stiff relative to one another.

More particularly, the flexibility or stiffness of sections 2 and 4 of lead 10 may be more accurately characterized as having different bending stiffnesses ($S_b$), wherein the ratio of the bending stiffness of stiff section 2 ($S_{bs}$) is at least 1.5 times that of the bending stiffness of flexible section 4 ($S_{bf}$). The bending stiffness ratios between more stiff sections 2 and more flexible sections 4 of lead 10 may also exceed about 1.5, about 1.8, about 2, about 2.2, about 2.4, about 2.6, about 2.8, about 3.0, about 4, about 5, about 6, about 7, about 8, about 9, about 10, about 20, about 30, about 40, about 50, about 100 or even greater.

Expressed mathematically, the ratio of bending stiffnesses of stiff sections 2 and flexible sections 4 of lead 10 of the present invention may be, by way of example only, the following:

$$1.5 \leq \frac{S_{bs}}{S_{bf}} \leq 100 \qquad \text{(eq. 1)}$$

$$1.5 \leq \frac{S_{bs}}{S_{bf}} \leq 20 \qquad \text{(eq. 2)}$$

$$2 \leq \frac{S_{bs}}{S_{bf}} \leq 10 \qquad \text{(eq. 3)}$$

$$2 \leq \frac{S_{bs}}{S_{bf}} \leq 5 \qquad \text{(eq. 4)}$$

When lead 10 is advanced through coronary sinus 13 into great cardiac vein 23 and then into posterior cardiac vein 17, for example, lead 10 will assume a winding, almost wave-shaped configuration, such that distal portion 22 is curved at the transition between coronary sinus 13 and posterior cardiac vein 17 as well as along the pathway of posterior cardiac vein 17.

It has been discovered that lead 10 will attempt to assume a position with minimal stored mechanical energy after having been implanted within veins 17 and 13. It has further been discovered that flexible sections 4 of lead 10 are most preferably located in those portions of the venous pathway having the curves of smallest radius (and therefore requiring the lowest amounts of stored potential mechanical energy).

Thus, first radius of lead body curvature 36 shown in FIG. 1 is most preferably located along those portions of lead 10 which comprise flexible portion 4 of lead body 12. Likewise, second, third and fourth radii of lead body curvatures 38, 40 and 42, respectively, shown in FIG. 2 are likewise located along portions of lead 10 comprising flexible portions 4. Relatively straight portions of lead 10, implanted within human heart 1 in a desired position preferably comprise relatively stiff portions 2 of lead body 12 as shown in FIG. 2.

In the present invention, therefore, moving flexible sections 4 from their locations within first, second, third and fourth curves 38, 40 and 42 requires that an axial force be exerted on lead 10 to advance lead 10 distally (i.e., exertion of a pushing force) or to retract lead 10 (i.e., exertion of a pulling force). Thus, owing to the unique variation of bending stiffness along the length and axial direction x of lead body 12 of lead 10, lead 10, once implanted, has a pronounced tendency to remain implanted and not to become dislodged from the cardiac vein within which it has been implanted.

Figure 3C:
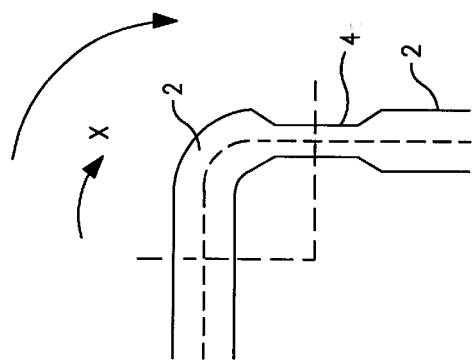
FIGS. 3A–3C illustrate various principles associated with bending stiffness in respect of several embodiments of the present invention.
Figure 3B:
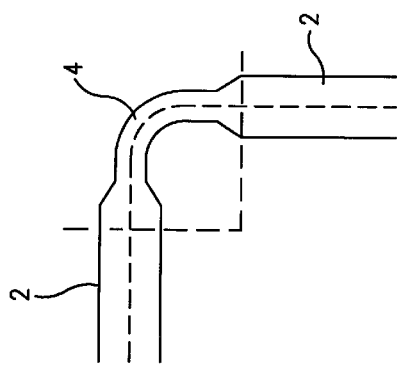
Figure 3A:
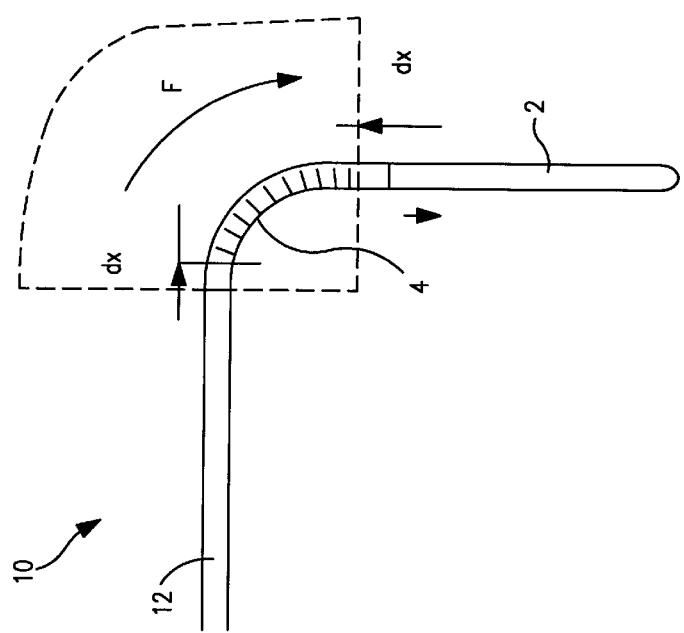

FIGS. 3A–3C illustrate various principles associated with the foregoing discussion concerning FIGS. 1 and 2. The principle of a relatively straight lead having variable bending stiffness as a function of lead position is based on two mechanical laws: (1) a mechanical body subjected to an external load or deformation assumes a shape which minimizes the potential mechanical energy stored in that body; and (2) variation of the stored potential energy in a body with displacement of the body results from an external force acting thereon. The external force (F) equals the derivative of energy (E) with respect to displacement (x) as shown below:

$$F = \frac{dE}{dx} \quad \text{(eq. 5)}$$

$$\frac{dE}{dx} = \frac{\varphi_b \cdot R_b}{R_b} \cdot \frac{dS_b}{dx} = \varphi_b \cdot \frac{dS_b}{dx} \quad \text{(eq. 6)}$$

where $S_b$=bending stiffness, $R_b$=bending radius and $\phi_b$ is the bend angle.

In FIG. 3A the additional energy stored in curved flexible section 4 of lead body 12 is defined by the force F required to displace lead 12 into the position shown along with the change in displacement dX. FIGS. 3B and 3C illustrate that the amount of bending energy required to bend lead body 12 through an approximate 90° curvature is greater for the geometry shown in FIG. 3C than is that illustrated in FIG. 3B. This is because stiff section 2 is located in the curved section of lead body 12 is FIG. 3C. Greater bending energy is therefore required to bend lead body 12 into the configuration shown in FIG. 3C than the configuration shown in FIG. 3B, where flexible section 4 is disposed along most of the curved section. In other words, the lead configuration shown in FIG. 3B is mechanically more stable than is the configuration shown in FIG. 3C because the configuration of FIG. 3B achieves a lower stored mechanical energy level.

Applying the law of minimum stored mechanical energy to the distal section of lead 10, we can draw the following conclusions. When lead 10 is implanted in coronary sinus 13 and great cardiac vein 23, mechanical energy is stored in those curved sections of lead 10 which are located in the transition from coronary sinus 13 to coronary vein 23 or 17. Such stored mechanical energy is proportional to the stiffness of lead 10 and the length being curved, as well as to the curvature (which is the inverse of the bending radius). Assume that the curvature is determined mainly by the venous anatomy, that the angle or curvature is about 90° and that the bend radius is about 5 mm. Such a curve will be maintained by forces acting on both sides of the lead body. The energy stored in lead body 12 is proportional to the average stiffness in the curved section.

Because the stiffness in the curved section varies with the position of the lead along the curve, the average stiffness of the lead body disposed in the curve will change if the lead is moved along the curve or the curve is moved with respect to the lead. Thus, axial displacement x of lead 10 along the curve defined by the venous anatomy results in a change in stored mechanical energy. If a lead of the present invention has been implanted within the venous anatomy of a patient properly, additional energy from an external source (e.g., a physician pulling or pushing the lead along the axial direction x) will have to be provided to displace lead 10 from its preferred minimum stored mechanical energy position.

It has been discovered that it is preferred to locate the most flexible section of the lead in those portions of the venous anatomy which exhibit the greatest curvature (or minimum bend radii). In such a configuration, the stiffness of lead 10 increases both proximally and distally with respect to the flexible section disposed in the curved section, and thus the stored energy of the lead body will become greater if the lead is moved either distally or proximally, or the venous anatomy moves with respect to the lead either distally or proximally. Stored mechanical energy is maintained at a minimum when the flexible section remains in the center of the curve. This results in a stable mechanical equilibrium, which in turn requires that external force of sufficient magnitude be exerted on lead 10 to move it distally or proximally from its minimum stored mechanical energy position.

In accordance with some embodiments of the present invention, lead 10 may be configured to have one relatively stiff portion 2 adjoining a relatively flexible portion 4, or may have a series of alternating relatively stiff portions 2 and relatively flexible sections 4. The bending stiffness of adjoining sections may increase or decrease in step-wise fashion, or may increase or decrease monotonically, exponentially or logrithmically. The respective lengths of relatively stiff portions 2 and relatively flexible portions 4 may also be varied according to the particular venous anatomy in which lead 10 is to be implanted.

In one embodiment of the present invention lead 10 is substantially straight prior to implantation and exhibits variable stiffness in distal portion 22 thereof such that at least one flexible section 4 adjoins proximally disposed and adjacent stiff portion 2 and distally disposed and adjacent stiff section 2, respectively. Such a lead configuration exhibits a bilateral, stable equilibrium (see FIG. 4C).

In another embodiment of the present invention lead 10 has a single stiff section 2 disposed in distal portion 22 which has a relatively flexible section 4 disposed proximally therefrom and adjacent thereto. Such a lead configuration has a unilateral, mechanically stable equilibrium, wherein the bending stiffness junction between two sections 2 and 4 is optimally placed at either end of a curve in a venous anatomy (see FIG. 4B).

FIGS. 4A–4C illustrate the behavior of several selected embodiments of lead 10 of the present invention, where bending stiffness ($S_b$) of lead body 12 is varied as a function of lead axial position x. In each of FIGS. 4A–4C, the upper diagram illustrates bending stiffness $S_b$ as a function of lead axial position x, the middle diagram illustrates the derivative of stored mechanical energy E with respect to axial distance x, (such derivative of stored mechanical energy being proportional to the axial force $F_{ax}$ exerted by the lead), and the lower diagram illustrates a lead structure corresponding to the bending stiffnesses and axial forces illustrated thereabove. In all of FIGS. 4A–4C the distal tip of the lead is positioned at the right side of the diagrams, relatively stiff portions of lead 10 are indicated by numeral 2 and relatively flexible sections of lead 10 are indicated by numeral 4.

Referring now to FIG. 4A, the monotonic increase in bending stiffness begins at the junction between sections 4 and 2 and increases to a maximum at tip 50. Such a configuration results in an axial force ($F_{ax}$) being exerted by lead 10 as shown in the middle diagram. Here, as in other axial force diagrams which follow below, a positive axial force is one which acts to pull the lead in a distal direction, whereas a negative axial force acts to pull a lead in a proximal direction (i.e., out of the vein within which it has been implanted).

Referring now to FIG. 4B, there is shown a lead exhibiting a step-wise jump in bending stiffness which occurs at the junction between sections 2 and 4 thereof. Once distal-most stiff portion 2 has been pushed beyond the venous curve of interest, and flexible section 4 is disposed in such curve, the axial force ($F_{ax}$) exerted by distal portion 22 of lead 10 upon the venous anatomy is again positive and tends to retain the lead in the implanted position unless an axial pulling force operating in the proximal direction is exerted on lead 10 to pull lead 10 around the curve of interest to thereby overcome $F_{ax}$.

FIG. 4C shows lead 10 having a series of contiguous alternating relatively flexible and relatively stiff sections 2 and 4, respectively. Lead 10 shown in FIG. 4C exhibits a number of points of bilateral stability separated by a distance equal to the length of relatively flexible and relatively stiff sections 4 and 2, respectively. Such a lead configuration has the advantage that a tip or electrode thereof may be placed at any of several positions along one or more coronary veins. That is, the embodiment of lead 10 shown in FIG. 4C has a number of different minimum mechanical energy storage positions which it may assume within the venous anatomy of a patient. The relative lengths of relatively flexible portions 4 and relatively stiff portions 2 may be varied according to the radii of the different venous curves which are anticipated to be encountered during lead implantation.

Thus, if it is anticipated that lead 10 will be implanted in a portion of the venous anatomy which is characterized by tightly curved venous portions, lead 10 may be configured to have relatively short stiff and flexible sections 2 and 4, respectively, to provide optimal results. Contrariwise, in the event the venous anatomy to be encountered during the implantation process is expected to be characterized by relatively gently curves, lead 10 may be configured such that relatively stiff sections 2 and relatively flexible section 4 have longer lengths to thereby provide optimal results. Lead 10 may also be appropriately configured such that portions 2 and 4 are of appropriate differing lengths for small, medium, and large radii curves encountered by the same lead 10.

It is important to note that when relatively stiff portion 2 of lead 10 is disposed in or along a curved section of the venous anatomy, an unstable mechanical equilibrium associated with a local maximum of stored potential mechanical energy being disposed in the curve results. It is therefore desired in the present invention that lead 10 have alternating relatively flexible sections 4 and relatively stiff sections 2 located within the venous anatomy in such a way that relatively flexible sections 4 are located in at least the major curves thereof.

The principle of varying the bending stiffness of lead 10 as a function of axial distance x may also be expanded to cover circumstances where the bending stiffness ($S_b$) is symmetric and equal around each axis of bending, or asymmetric and unequal around each axis of bending.

Figure 5A:
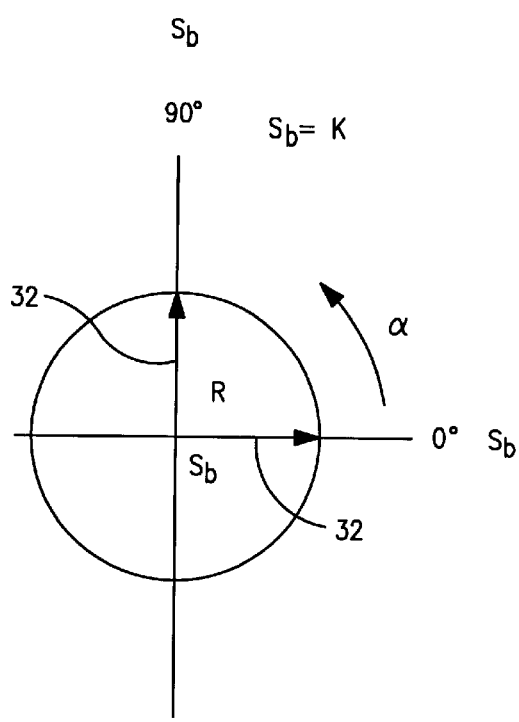
FIGS. 5A and 5B show two different embodiments of a lead body of the present invention in cross-section.
Figure 5B:
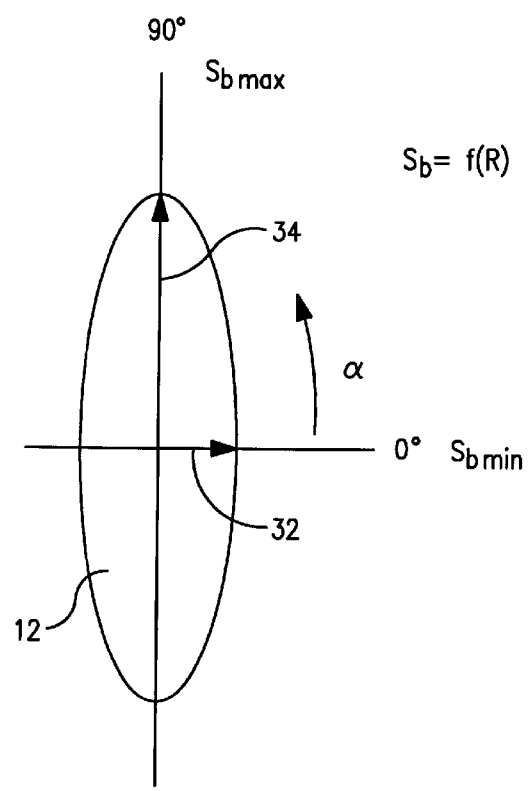

Referring now to FIGS. 5A and 5B, there are shown in cross-section lead body 12 exhibiting symmetric equal bending stiffnesses around each axis of bending in FIG. 5A and lead body 12 having asymmetric unequal bending stiffnesses around each axis of bending in FIG. 5B. Thus, lead 10 shown in FIG. 5A may be bent in any direction from 0° to 360° without any change in bending moment being required. Contrariwise, lead 10 shown in FIG. 5B requires more bending moment when lead 10 is bent in the directions of 0° and 180°, while less bending moment is required when lead 10 is bent in the 90° and 270° directions.

Figure 6A:
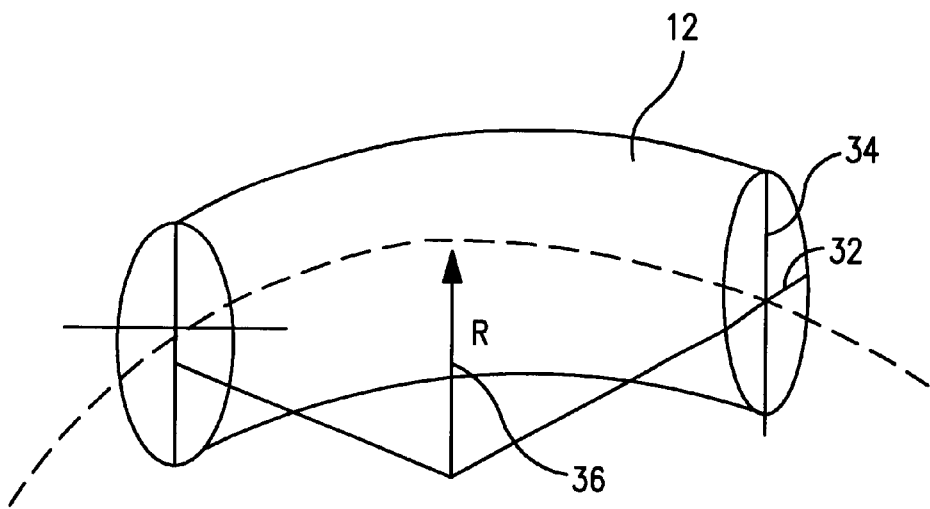
FIGS. 6A and 6B illustrate combined cross-sectional and perspective views of two different lead bodies of the present invention.
Figure 6B:
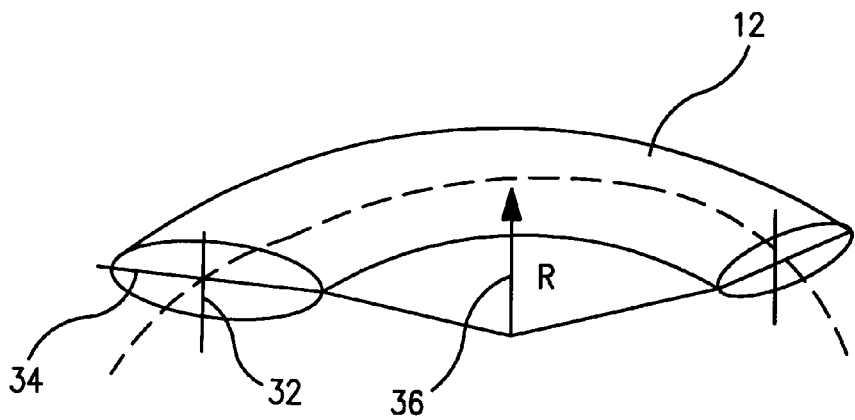

FIGS. 6A and 6B illustrate lead bodies which require asymmetric bending moments as a function of angular direction. In order to maintain minimal mechanical energy, lead body 12 illustrated in FIG. 5B will attempt to orient itself along the plane of the curve within which it is disposed such that bending preferentially occurs over the lead axis along the most flexible lead cross-section (e.g., the 90° and 270° orientations). This characteristic may be exploited so that lead body 12 may be oriented such that an electrode disposed along or near such a section exhibiting asymmetric bending stiffness is strategically placed within a vein. Thus, for example, a pacing or defibrillation electrode 14 disposed near such an asymmetric bending stiffness section may be oriented towards the myocardium (which may be beneficial in obtaining low pacing thresholds and improved sensing of signals).

FIG. 6A illustrates the natural orientation which the lead of FIG. 5B will assume within a curved portion of the venous anatomy. The lead configuration shown in FIG. 6B is one which requires maximum mechanical energy and therefore will not be assumed by lead 10 when disposed in a curved section of the venous anatomy.

Figure 7:
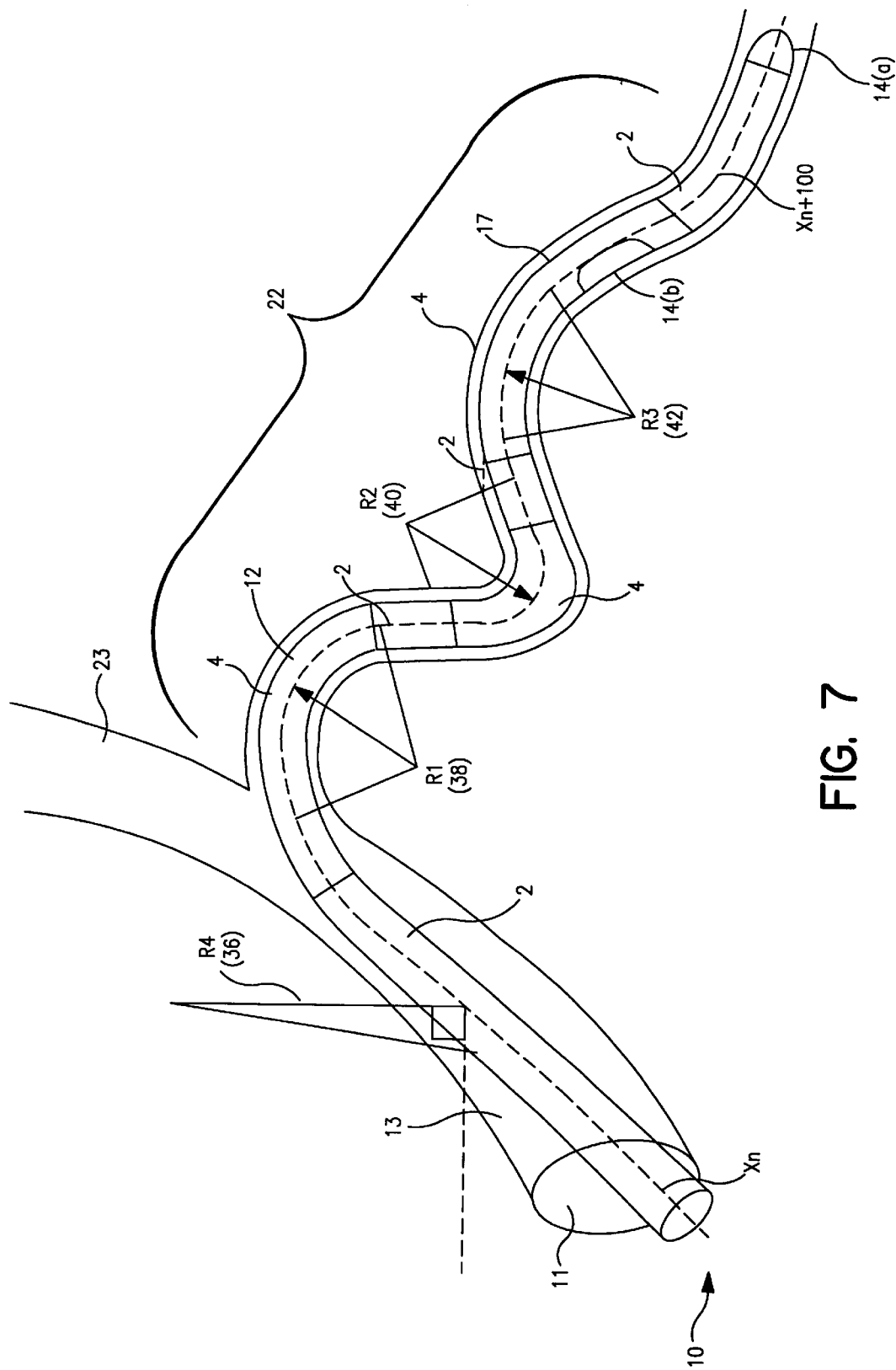
FIG. 7 illustrates an enlarged cross-sectional view of one embodiment of a lead of the present invention disposed within portions of the venous anatomy.

Referring now to FIG. 7, there is shown an enlarged cross-sectional view of lead 10 disposed within posterior cardiac vein 17 after having been routed through coronary sinus 13. FIG. 7 shows how venous vasculature exhibits curves having radii which alternate in direction and magnitude. Bending of lead body 12 along posterior cardiac vein 17 occurs substantially within a single plane (i.e. $R_1$, $R_2$ and $R_3$ are disposed substantially in the same plane). Because radii $R_1$, $R_2$ and $R_3$ are so much smaller than radius $R_4$, more radical bending of lead 10 is required in posterior cardiac vein 17. Bending of lead body 12 occurring along $R_4$ of coronary sinus 13 occurs in a plane which is approximately perpendicular to the plane along which $R_1$, $R_2$ and $R_3$ are disposed. Note that $R_4$ is substantially longer than $R_1$–$R_3$ and thus the curve of coronary sinus 13 is not only along a different plane but of substantially less magnitude. Consequently, a preferential orientation of lead 10 is determined principally by radii $R_1$–$R_3$ rather than by radius $R_4$. This, in turn, means that a lead having an asymmetric cross-sectional configuration or bending stiffness which varies asymmetrically as a function of cross-sectional angular position may be successfully employed to ensure the retention of lead 10 within a desired portion of the venous anatomy. For example, lead 10 may be configured to have a first asymmetric cross-sectional configuration for implantation along the distalmost portions of a selected cardiac vein in a first preferred orientation where bending radii are small, and to have a second asymmetric cross-sectional configuration for implantation in or along more proximally disposed portions of the venous anatomy and in a second preferred orientation, wherein the first and second orientations are different owing, for example, to the first and second cross-sections being angularly rotated in respect of one another.

Assuming the embodiment of the present invention illustrated in FIGS. 5B and 6A is employed for implantation within a desired portion of the venous anatomy, such a lead will have two orientations where stored mechanical energy will be achieved, namely at φ=90° or φ=270°, assuming that the bending stiffness of the lead is equal in those opposite directions. Electrode 14(*b*) may be positioned on one side or the other of lead body 12 to stimulate a desired portion of the heart as shown in FIG. 7. Such positioning may be confirmed through the use of x-ray or echo identification of the orientation of electrode 14(*b*). If required, lead 10 may be rotated through 180° such that electrode 14(*b*) faces a desired direction.

FIG. 8A illustrates lead 10 of the present invention having multiple electrodes 14 of the present invention disposed thereon. More particularly, lead 10 comprises pacing electrodes 14*c*, 14*b* and 14*d* as well as coil defibrillation electrode 14*a*. Beneath lead 10 in FIG. 8A are shown FIGS. 8B and 8C exhibiting two different examples of possible bending stiffness profiles. The bending stiffness profile exhibited in FIG. 8B has only a single portion 4 of decreased flexibility adjoining two relatively stiff sections 2 located proximally and distally in respect thereof. Contrariwise, the bending force profile illustrated in FIG. 8C exhibits an alternating sequence of relatively flexible sections 4 and relatively stiff sections 2. As noted above, flexible sections 4 of lead 10 are optimally positioned along portions of the venous anatomy which exhibit the greatest curvature to thereby retain lead 10 within a desired portion of a cardiac vein.

FIG. 9A shows another embodiment of lead 10 of the present invention, where pacing electrodes 14c and 14b are located proximally and distally from coil defibrillation electrode 14a. FIGS. 9B and 9C illustrate two examples of bending stiffness profiles for the lead of FIG. 9A, where bending stiffness varies as a function of axial distance X in the manner shown.

When lead 10 is characterized in having the bending stiffness of FIG. 9B, distal section 22 of lead 10 prevents lead 10 from pulling back into the coronary sinus after it has been implanted within the desired coronary vein. The bending stiffness profile of FIG. 9B does not result, however, in a lead which exhibits or provides a stability point for lead advancement.

In that regard, a more preferred design is one exhibiting the bending stiffness profile shown in FIG. 9C, where a section of increasing stiffness 47 precedes or forms part of distal portion 22 of lead 10 such that section 47 is disposed in the right atrium and coronary sinus upon implantation. Such an increase in bending stiffness as a function of axial distance x, where bending stiffness increases as one moves towards the distal end of lead 10, causes lead 10 to be pushed deeper into the coronary sinus.

The length of section 47 optimally ranges between 5 cm and 15 cm in length and is most preferably about 10 cm. Other lengths of section 47 are, of course, contemplated in the present invention, and include, but are not limited to, the following ranges of lengths: between 2 cm and 17 cm, between 7 cm and 13 cm, and between 9 cm and 11 cm. Likewise, the length of section 47 may exceed 15 cms and may be less than 2 cms. The general principle respecting section 47 is that it exhibit an increase in stiffness over a predetermined length of lead 10. Note, however, that the manner in which bending stiffness increases may be monotonic, gradual, step-wise, exponential, or logrithmic.

For the present invention to function properly in the environment of the human body, it is important that the mechanical stiffness properties of the materials employed to construct lead 10 remain stable over time after the lead has been implanted. Moreover, the materials from which lead 10 are constructed must, of course, be biostable and biocompatible. In a preferred embodiment of the present invention, lead 10 is formed of materials exhibiting bending stiffnesses which remain relatively unaffected by the effects of implantation within the human body for a period of time sufficient to permit the lead to become embedded and encapsulated within the venous anatomy to thereby provide sufficient chronic lead stability over time. In such a manner, stress relaxation of the materials from which lead 10 is formed may be permitted in the region of the lead exhibiting multiple stiffness regimes.

It is well know that metal parts such as electrode surfaces tend to maintain their mechanical properties over time. Polymeric materials from which lead body 12 is customarily formed, however, may exhibit low grade creep characteristics (e.g., low stress relaxation), and may therefore exhibit bending modulii which are not dependent on temperature or fluid saturation. In order not to lose the desired bending stiffness properties of the present invention to the extent that destabilization might occur after implantation, materials for forming lead body 12 of the present invention include silicone rubber and polyurethane. Other implantable grade materials are, of course, contemplated in the present invention, including but not limited to, PEBAX, PTFE,and ETFE.

I refer now to FIGS. 10A–10M, where different embodiments of the present invention are illustrated, all of which exhibit variations in bending stiffness of lead body 12 as a function of axial distance x.

Figure 10A:
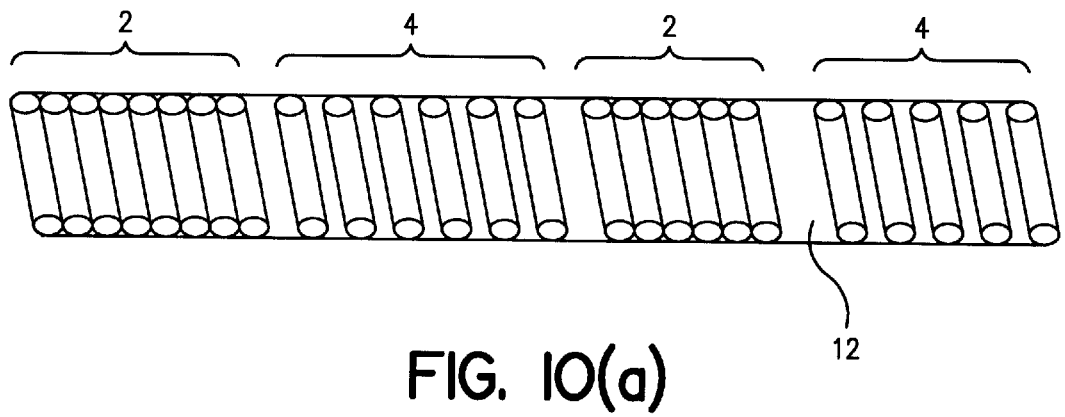
FIGS. 10A–10M illustrate several different embodiments of the present invention exhibiting variations in bending stiffness of the lead body as a function of axial distance.

FIG. 10A illustrates one embodiment of the present invention where coils having variable pitch are embedded within lead body 12 to thereby impart variations in bending stiffness to lead body 12 as a function of axial distance x. Tightly wound pre-stressed coils are disposed along relatively stiff sections 2, while loosely wound coils are disposed in relatively flexible sections 4. Note that the coils shown in FIGS. 10A–10C. may, of course, be employed in conjunction with or as a part of defibrillation electrodes or electrical conductors, or in conjunction with pacing or sensing electrodes or electrical conductors.

Figure 10B:
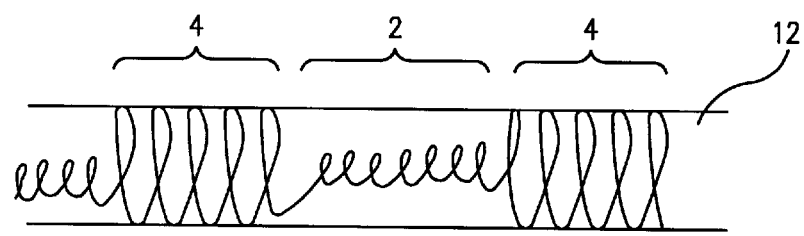

FIG. 10B illustrates one embodiment of the invention where the diameter of the coils disposed within lead body 12 is varied to thereby impart variations in bending stiffness to lead body 12 as a function of axial distance x. Large diameter coiled portions form relatively flexible portions 4, while small diameter coiled portions form relatively stiff portions 2.

Figure 10C:
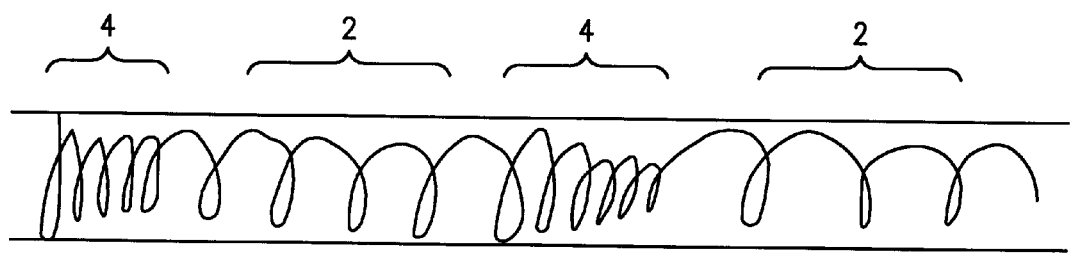

FIG. 10C illustrates another embodiment of the present invention where variations in coil pitch are employed to impart variations in bending stiffnesses to lead body 12 as a function of axial distance x. Low pitch sections form relatively flexible portions 4 while large pitch sections form relatively stiff sections 2. Both sections 2 and 4 are most preferably space wound. Of course, combinations of FIGS. 10A, 10B and 10C also fall within the scope of the present invention.

Figure 10D:
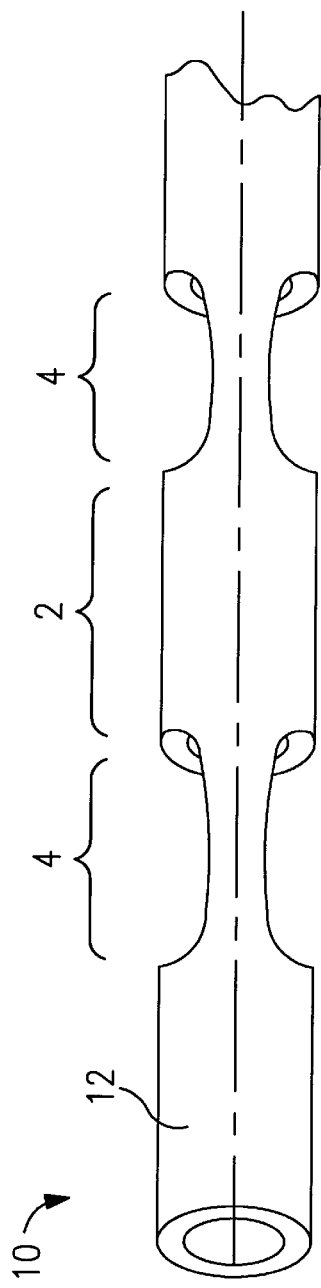

FIG. 10D illustrates an embodiment of the present invention where portions of lead body 12 are carved, ablated or otherwise removed from lead body 12 or not included therein during formation to create preferentially oriented relatively flexible sections 4 adjoining relatively rigid sections 2.

Figure 10E:
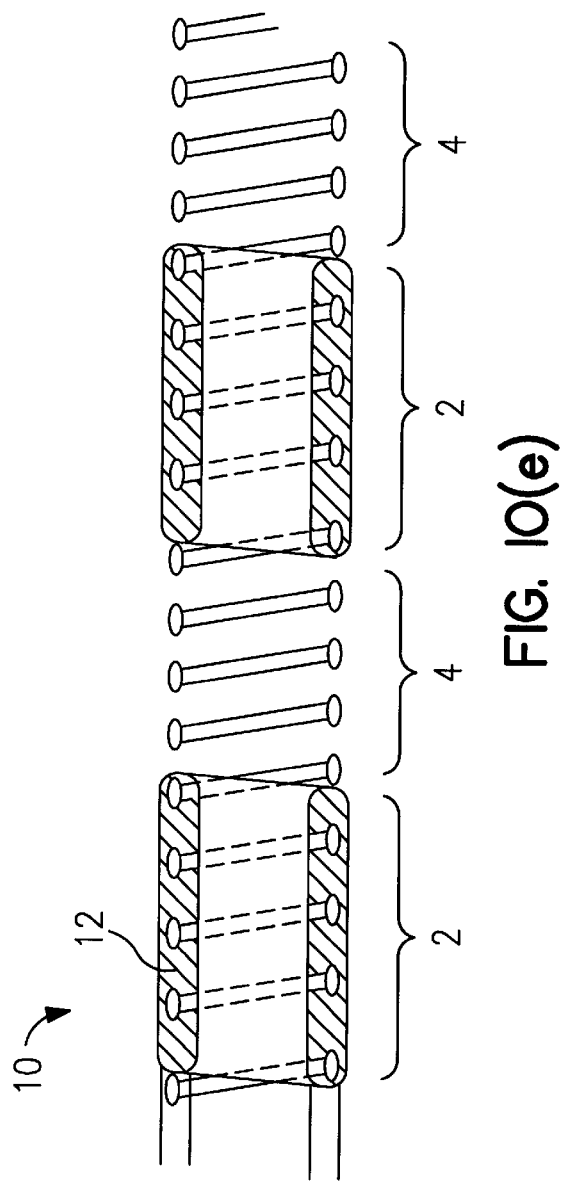

FIG. 10E illustrates one embodiment of the present invention where coils disposed in lead body 12, and which may constitute or form part of one or more pacing, sensing or defibrillation electrodes or electrical conductors, are embedded in a relatively stiff material such as a polymeric substance.

The relatively stiff sections within which the coils are embedded exhibit increased bending stiffness relative to those sections of lead body 12 where the coils are not embedded within the relatively stiff material.

Figure 10F:
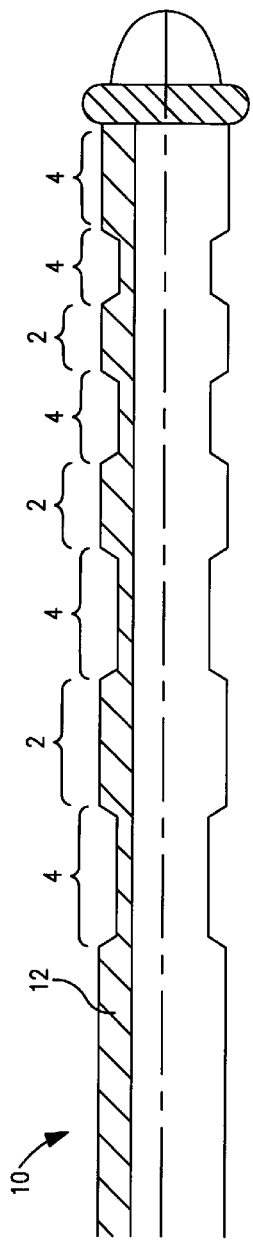

FIG. 10F illustrates one embodiment of the invention where variations in the thickness or type of lead body insulation are employed to impart variations in bending stiffness to lead body 12 as a function of axial distance x.

Figure 10G:
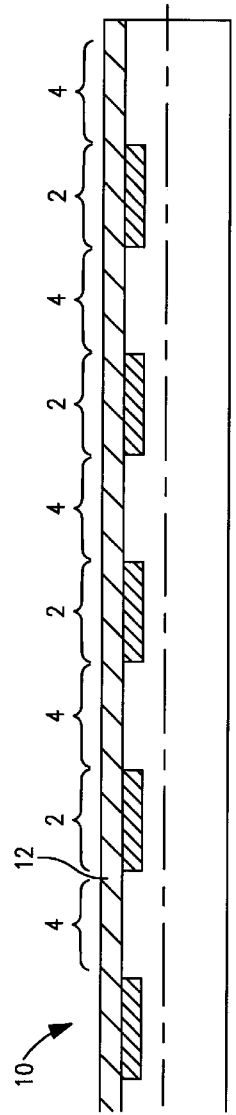

FIG. 10G illustrates one embodiment of the present invention where increased rigidity is imparted to certain sections of lead body 12 by disposing ring shaped relatively stiff members beneath the outer insulation of lead 10, and where the relatively stiff members adjoin relatively flexible portions of lead body 12.

Figure 10H:
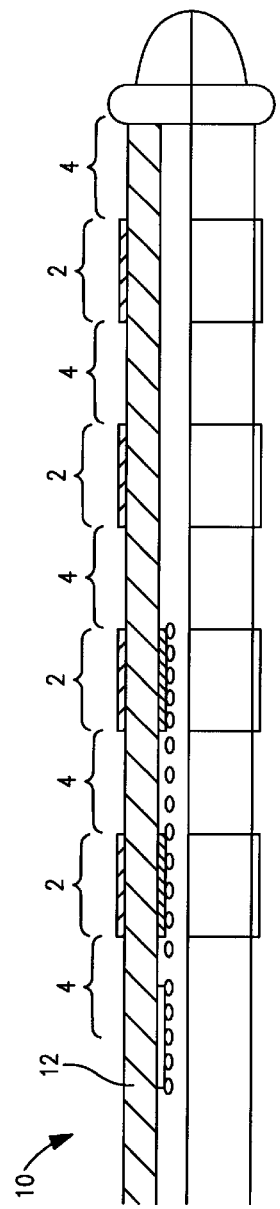

FIG. 10H illustrates one embodiment of the present invention where relatively stiff members are positioned on the outside of the outer insulation of lead body 12 to thereby impart variations in bending stiffness to lead body 12 as a function of axial distance x. Note that relatively stiff members 2 shown in FIGS. 10G and 10H may include electrodes or electrode surfaces specifically designed and adapted for the purpose of not only stimulating the heart but also to provide variations in bending stiffness as a function of axial distance x according to the particular design parameters corresponding to the portion of the venous anatomy within which lead 10 is to be disposed.

Figure 10I:
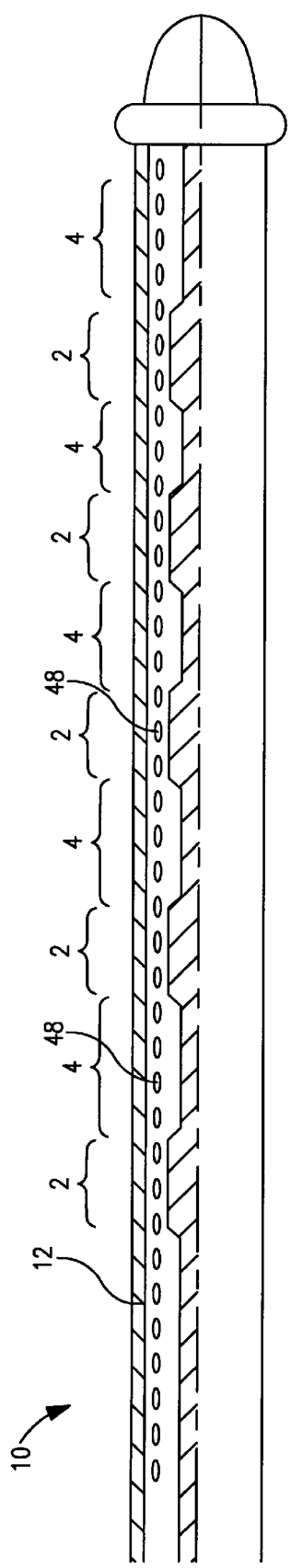

FIG. 10I illustrates one embodiment of the present invention where an electrical conductor coil 48 is disposed about an internal member exhibiting bending stiffnesses which vary as a function of axial distance x owing to increased thicknesses over relatively stiff sections 2 and decreased thicknesses over relatively flexible sections 4.

Figure 10J:
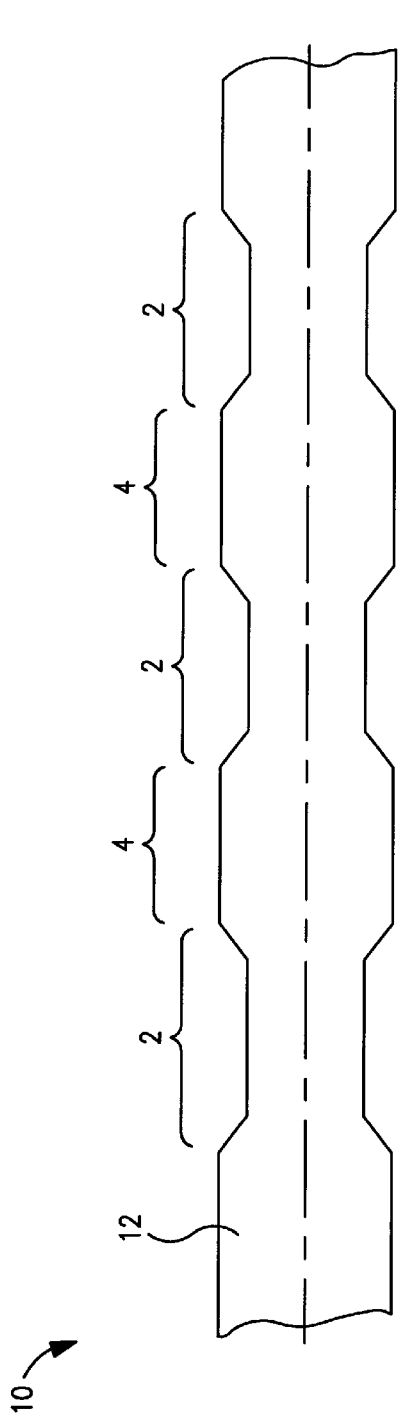

FIG. 10J illustrates one embodiment of the present invention where opposing sections of tubing forming lead body 12 are flattened without perforating or making holes in the tubing to thereby impart increased flexibility to lead body 12 along one direction.

Figure 10K:
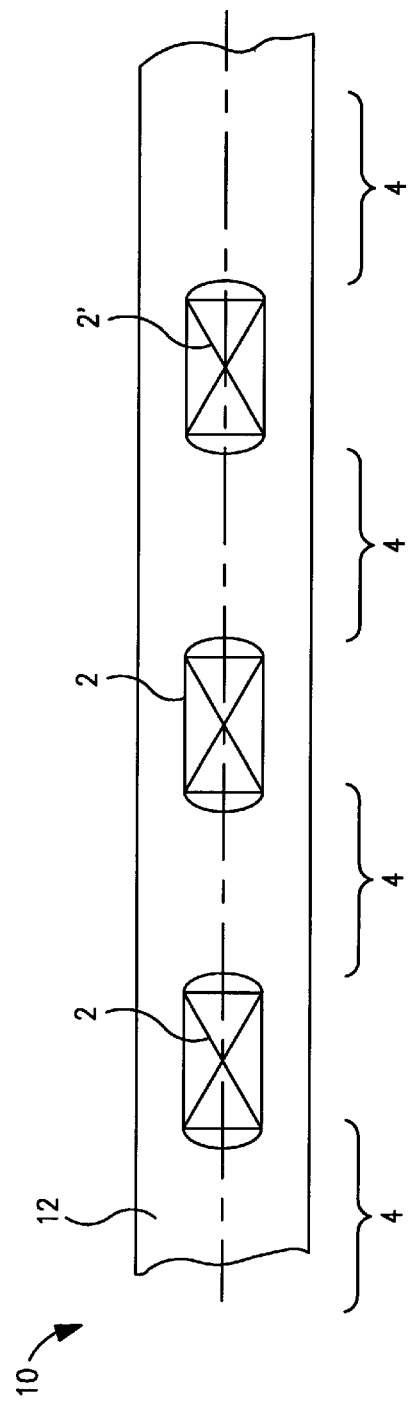

FIG. 10K shows the lead body illustrated in FIG. 10J rotated through 90° such that flattened portions 2 are viewed from above.

Figure 10L:
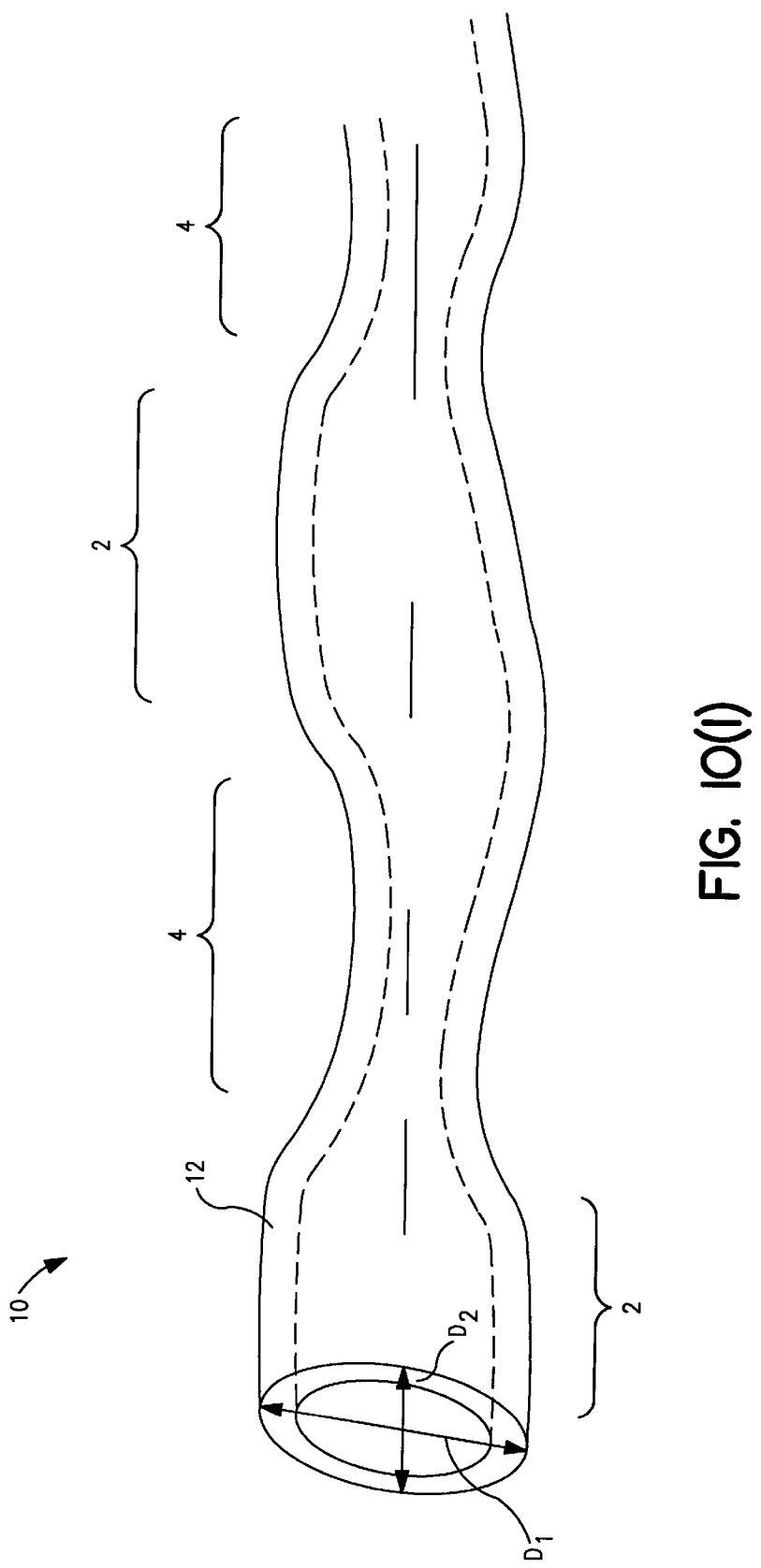
Figure 10:
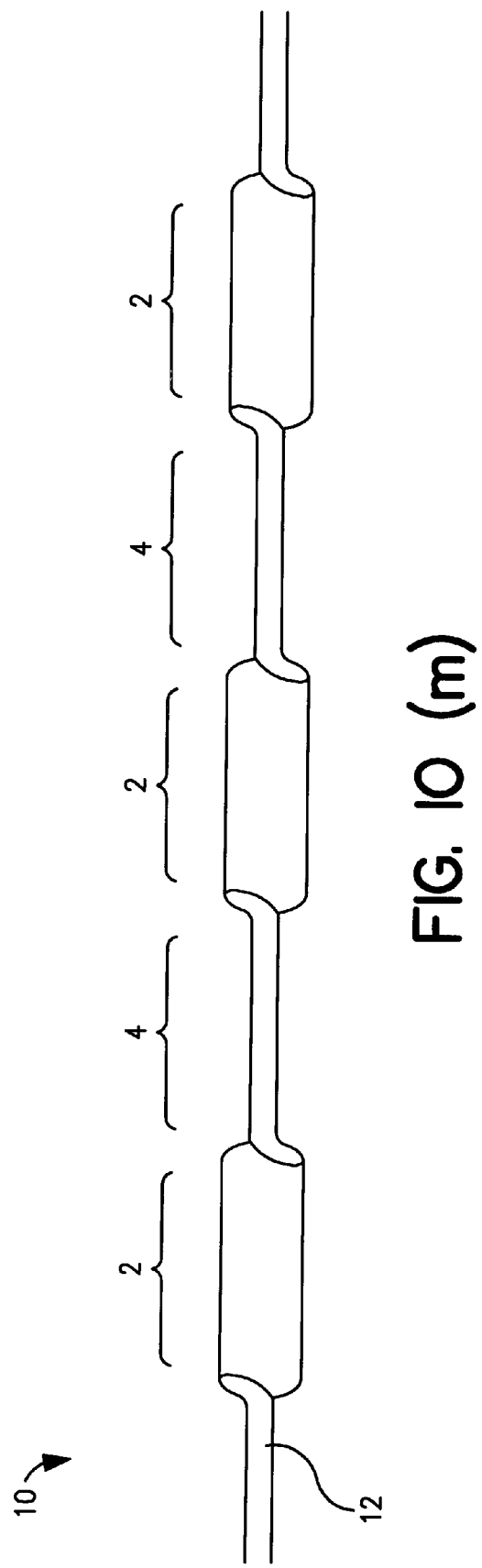

FIG. 10L illustrates one embodiment of the present invention where the diameter of lead body 12 and/or the thickness of an outer layer forming part of lead body 12 is varied as a function of axial distance x to thereby impart variations in bending stiffness as a function of axial distance x. In the embodiment of the present invention illustrated in FIG. 10L, not only may the diameter of lead body 12 be varied to impart changes in bending stiffness as a function of axial distance x, but also such variations may be effected in asymmetric manner such that lead body 12 is radially asymmetric in cross-section and has a preferential bending axis which will preferentially be disposed along the vein within which it is implanted.

FIG. 10M illustrates yet another embodiment of the present invention, where lead body 12 has incorporated therein a flat rivet shaped material which is twisted along pre-selected portions thereof to provide preferential orientation of lead 10 when implanted within the human body. Alternating portions 2 and 4 may be of such lengths and orientations as to provide one or more preferred orientations for lead 10 within the venous anatomy according to the particular requirements at hand, e.g., implantation within the middle cardiac vein, great cardiac vein, coronary sinus, oblique left atrial vein, small cardiac vein, and/or posterior cardiac vein.

FIG. 10M shows another embodiment of the present invention where lead 10 exhibits variations in bending stiffness along axial direction x. Flattened portions 2 interposed between relatively flexible portions 4 provide increased stiffness or rigidity to sections 2. Relatively stiff sections may also serve to orient electrodes 14 (not shown) such that electrodes 14 may be positioned to stimulate a selected portion of the heart more efficiently, as well as to provide improved sensing of intra-cardiac signals.

It is contemplated in the present invention that means of varying the bending stiffness of the distal section of a lead of the present invention other than those described here and above respective FIGS. 10A–10M fall within the scope of the present invention. For example, the material from which lead body 12 is formed may be varied compositionally or otherwise as a function of axial distance x, to thereby effectuate changes in the bending stiffness thereof. The degree to which a polymer forming lead body 12 is cross-linked may be varied as a function of axial distance x. The density of the polymers 5 or other materials employed to form lead body 12 may be varied as a function of axial distance x. The molecular weight of the polymers or other materials from which lead body 12 is formed may be varied as a function of axial distance x. A flexible tubular member containing a shape-memory tube may be included in a lumen extending along a central axis of the lead body, and a control system may then selectively heat portions of the shape-memory tube to change the bending stiffness or shape thereof. The foregoing and other methods of varying the bending stiffness of the distal section of a lead body of the present invention are contemplated in the present invention. See, for example, U.S. Pat. No. 5,437,632 for "Variable stiffness balloon catheter"; U.S. Pat. No. 5,499,973 for "Variable stiffness balloon dilatation catheters"; U.S. Pat. No. 5,531,685 for "Steerable variable stiffness device"; U.S. Pat. No. 5,639,276 for "Device for use in right ventricular placement and method for using same"; U.S. Pat. No. 5,833,604 for "Variable stiffness electrophysiology catheter"; and U.S. Pat. No. 5,733,496 for "Electron beam irradiation of catheters to enhance stiffness", the disclosures of which are hereby incorporated by reference herein, each in its respective entirety.

Figure 11A:
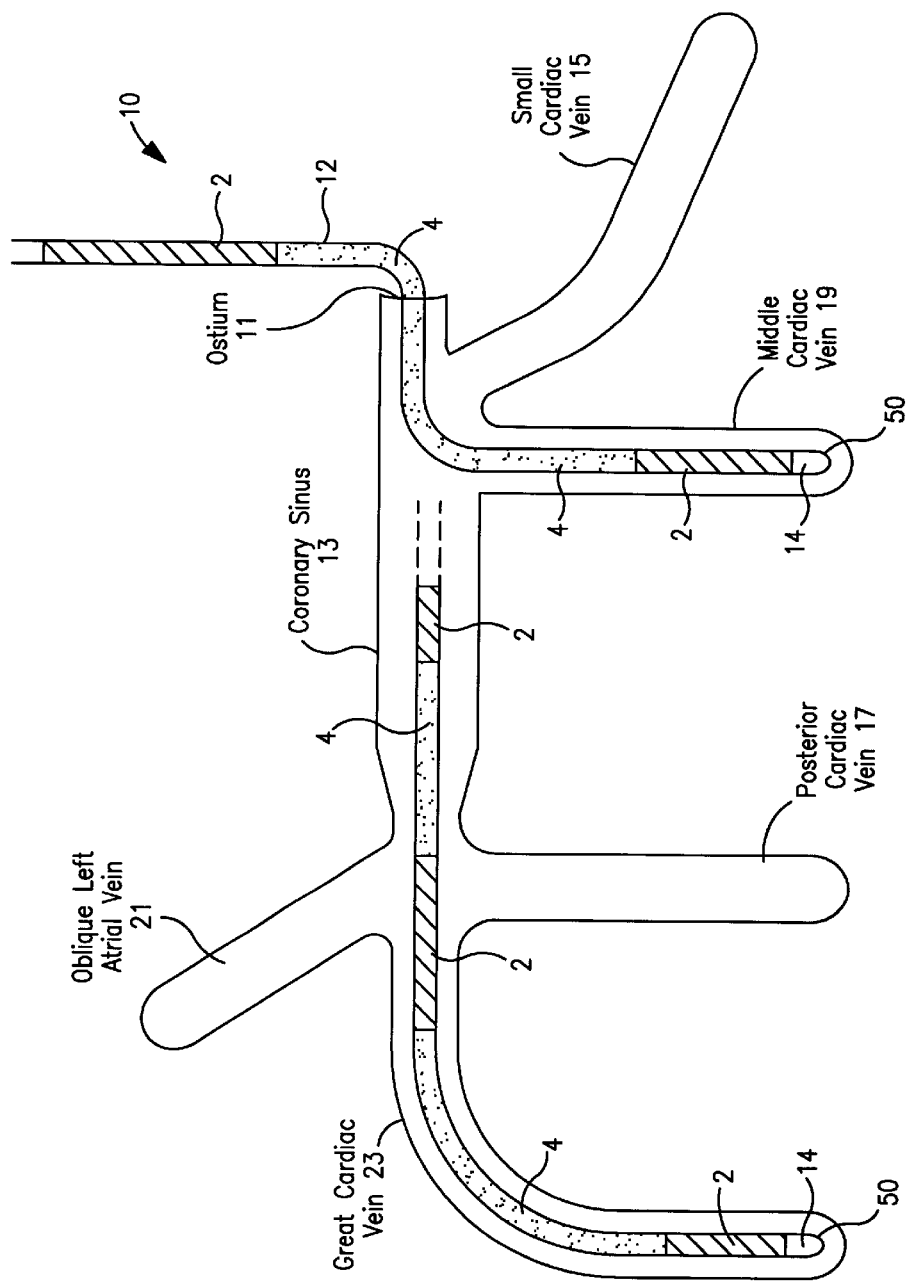
FIGS. 11A–11D is a stylized cross-section of the venous anatomy within which various embodiments of the present invention may be implanted.

FIG. 11A is a stylized cross-section of the venous anatomy with which the present invention is principally concerned. Note that the various veins are illustrated stylistically and are not shown to scale. In FIG. 11A, one lead of the present invention is shown disposed in great cardiac vein 23 such that distalmost relatively rigid section 2 is located near the distal end of great cardiac vein 23. Distalmost relatively flexible section 4 is located immediately proximal from distalmost section 2 and is disposed along that portion of great cardiac vein 23 exhibiting the greatest curvature. Other sections 2 and 4 located proximally from distalmost relatively flexible section 4 are also shown in FIG. 11A. The lead geometry shown in FIG. 11A results in better retention of lead 10 within great cardiac vein 23 than would otherwise be achieved owing to the differences in stiffness of sections 2 and 4.

Continuing to refer to FIG. 11A, but now to the right portion thereof, there is shown medical electrical lead 10 implanted within Middle cardiac vein 17. Once again, distalmost relatively stiff section 2 is located near the distalmost portion of posterior cardiac vein 17, while distalmost relatively flexible section 4 is disposed in those portions of the venous anatomy which exhibit the greatest curvature (e.g., ostium 11 and the entry to middle cardiac vein 19).

Like medical electrical lead 10 shown implanted in great cardiac vein 23 of FIG. 11A, medical electrical lead 10 shown implanted in middle cardiac vein 19 is retained therein through the action of alternating relatively stiff and relatively flexible sections 2 and 4, respectively, where flexible sections 4 are disposed along those portions of the venous anatomy exhibiting the greatest curvature and relatively stiff portions 2 are disposed in those portions of the venous anatomy exhibiting the least curvature.

Continuing to refer to FIG. 11A, it is to be noted that lead 10 of the present invention may be implanted in any of the veins shown in FIG. 11A, as well as in any other suitable vein for pacing and/or defibrillating heart 1 of a patient. Moreover, it is important to note that the present invention may be employed such that the distalmost portion thereof need not necessarily be positioned at the distalmost portion of a selected cardiac vein. That is, the distalmost portion of medical electrical lead 10 of the present invention may be located wherever it is determined to be appropriate to place lead 10.

The present invention lends itself well to pacing and/or defibrillating heart 1 in various manners or modes. More particularly, if a patient's left atrium or left ventricle is to be paced and/or defibrillated, lead 10 and its electrodes may be appropriately positioned within coronary sinus 13. If a patient's left ventricle is to be paced and/or defibrillated, lead 10 of the present invention may be appropriately positioned in great cardiac vein 23 or posterior cardiac vein 17, most preferably at the distal ends thereof. Both of a patient's ventricles may be paced and/or defibrillated if medical electrical lead is appropriately implanted within middle cardiac vein 19. Location of lead 10 of the present invention within oblique left atrial vein 21 can result in successful pacing or defibrillation of the left atrium. Location of the pacing and/or defibrillation electrodes of lead 10 of the present invention near the middle portions of great cardiac vein 23 can result in pacing and/or defibrillation of the right ventricle, or even pacing and/or defibrillating both the right and left ventricles.

Figure 11B:
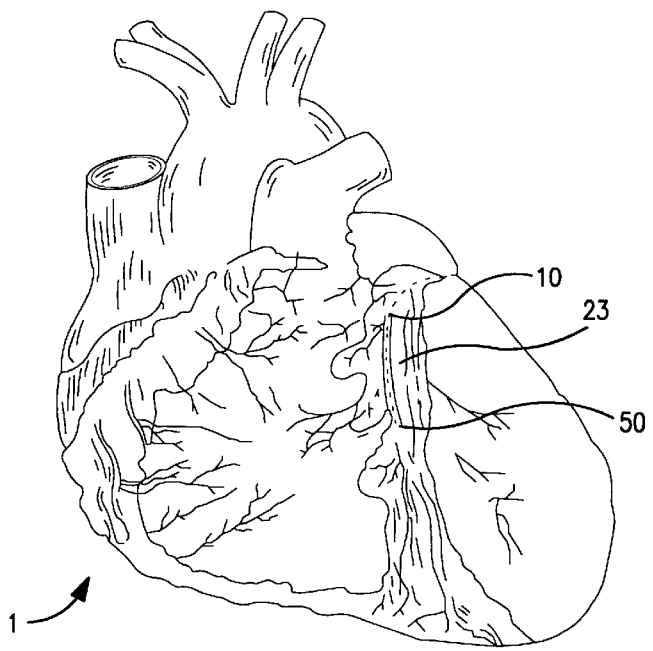
Figure 11C:
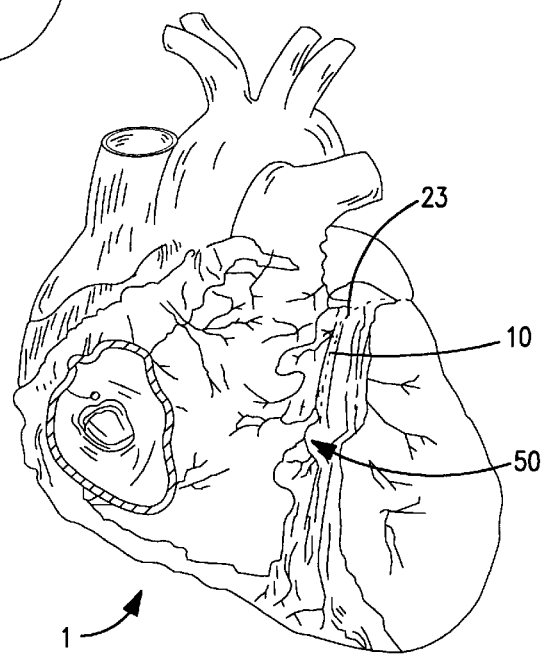
Figure 11D:
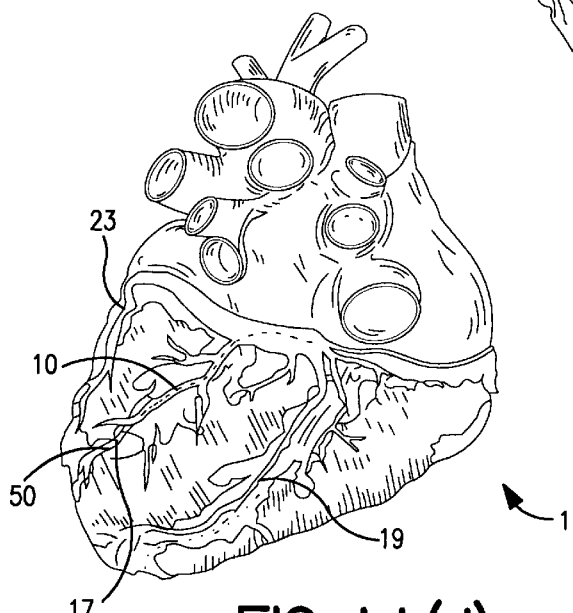

FIGS. 11B–11D illustrate positioning of lead 10 within various coronary veins according to various methods of pacing and/or defibrillating. FIG. 11B shows one embodiment of lead 10 of the present invention positioned within the anterior cardiac vein in a location suitable for pacing the left atrium. FIG. 11C shows one embodiment of lead 10 of the present invention located in a position suitable for pacing the left ventricle from the posterior cardiac vein. FIG. 11D shows one embodiment of lead 10 of the present invention positioned within the posterior cardiac vein such that a first electrode is aligned with the left atrium and the second electrode is aligned with the left ventricle.

Figure 12A:
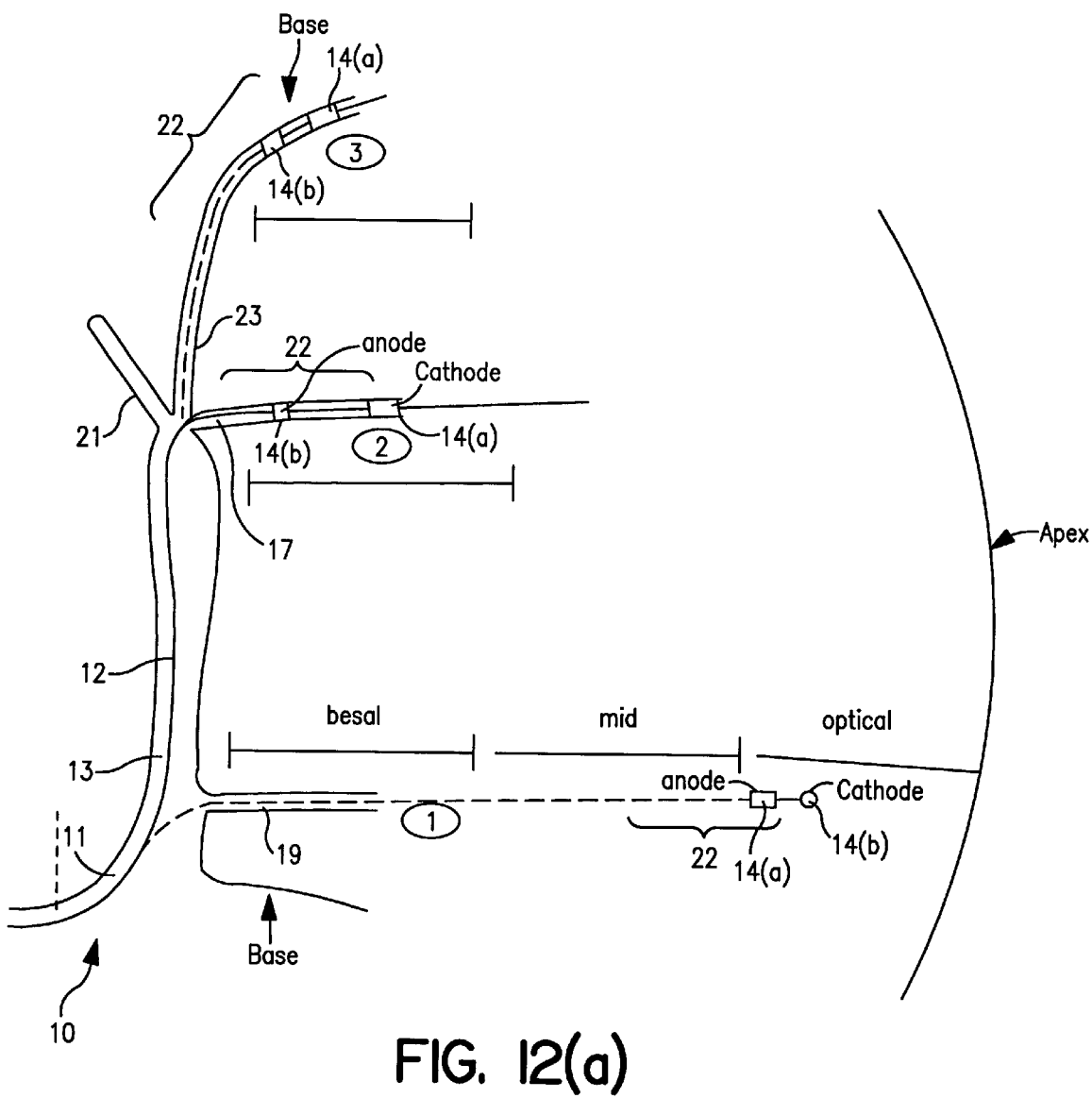
FIG. 12A illustrates three different positions within which various embodiments of the present invention may be located within the human heart.

FIG. 12A illustrates still further embodiments of the present invention and methods of practicing same. In FIG. 12A, three different positions for various embodiments of medical electrical lead 10 of the present invention are shown: (1) for apical pacing of the heart, and (2) and (3) for basal pacing or other stimulation of the heart. Lead 10 shown positioned within middle cardiac vein 19 has cathode 14(b) and anode 14(a) disposed near distal end 22 thereof for effecting apical pacing and/or defibrillation of heart 1. Medical electrical lead 10 of the present invention shown implanted in posterior cardiac vein 17 is positioned such that anode 14(a) and cathode 14(b) may pace and/or defibrillate the heart from a more basal position. Similarly, lead 10 shown implanted in great cardiac vein 23 has electrodes 14(a) and 14(b) positioned for basal pacing and/or defibrillation of heart 1.

Note that in many of the embodiments of the present invention shown herein, that any of the electrodes illustrated may serve as an anode or cathode depending on the particular requirements and applications at hand. Likewise, unipolar or bipolar arrangements of the electrodes are contemplated in the present invention, as well as utilization of portions of cardiac stimulator 30 as yet another electrode.

Basal stimulation of heart 1 is known to provide superior hemodynamic results under certain circumstances as a result of pacing. Similarly, in a bipolar configuration where both electrodes 14(a) and 14(b) are located in a coronary vein, the signals sensed thereby can provide superior discrimination between atrial and ventricular signals.

As discussed hereinabove, asymmetrical bending stiffness directions of lead body 12 may be employed to orient placement of stimulating electrodes 14(a) and 14(b) such that they are pressed against or directed towards the myocardium or other selected portions of heart 1.

Figure 12B:
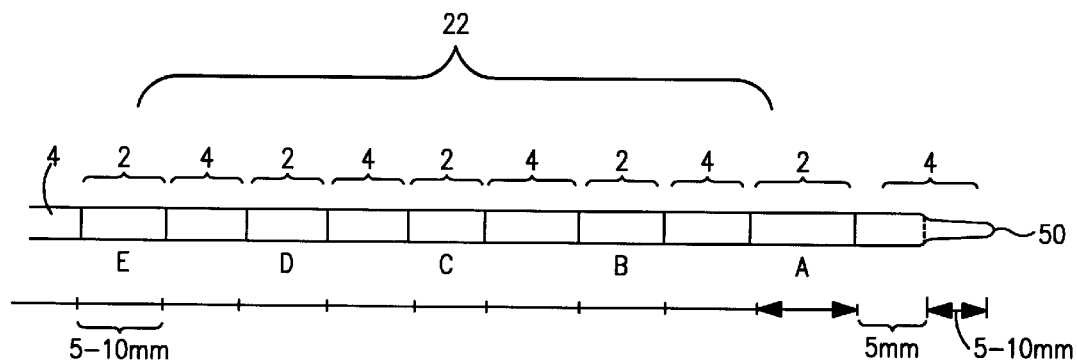
FIGS. 12B–12D illustrate several preferred embodiments of the present invention.
Figure 12C:
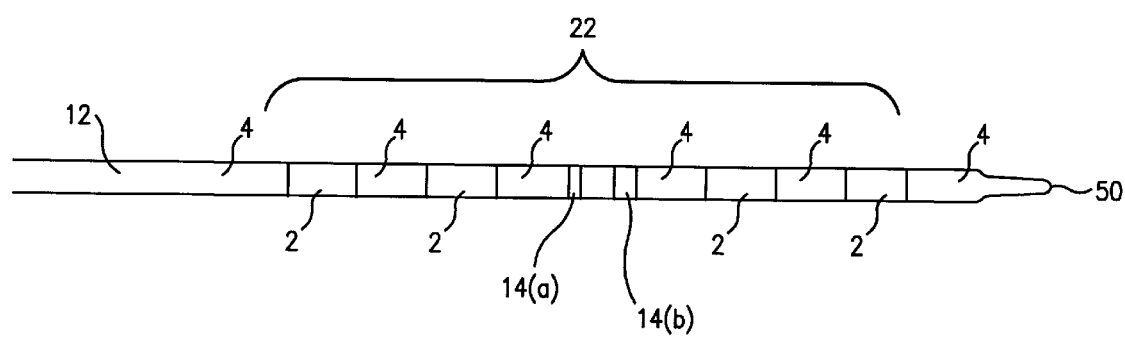
Figure 12D:
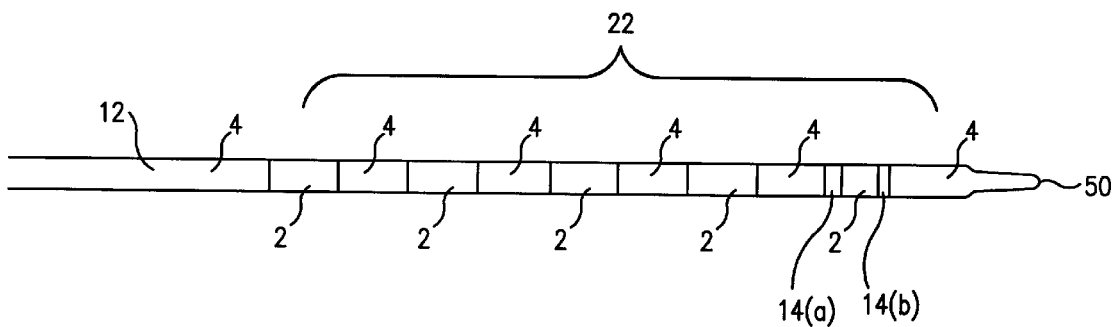

FIGS. 12B–12D show further preferred embodiments of the present invention. In FIG. 12B, no electrodes are shown for the purpose of facilitating discussion therof. In FIG. 12B, relatively stiff sections 2 are disposed between and alternate with relatively flexible sections 4. The axial lengths of sections 2 and 4 are optimally about 8 mm, or between about 5 mm and about 10 mm in length, or any other suitable length required to practice the present invention. Those portions of lead 10 disposed in coronary sinus 13 are most preferably relatively flexible sections 4. Tip 50 is most preferably tapered. In preferred embodiments of the present invention, there are three to five relatively stiff sections. The length of relatively stiff sections 2 varies optimally between about 5 mm and about 12 mm. However, distalmost relatively stiff section of lead 10 of the present invention may range between about 5 mm and about 50 mm in length, inclusive.

The diameter of lead 10 of the present invention most preferably ranges between about 1 mm and about 2 mm, but may be as small as about 0.5 mm and as large as about 3 mm or even larger. The length of relatively flexible sections 4 most preferably ranges between about 5 mm and about 12 mm in length, and is preferably about 8 mm long. Electrodes are most preferably placed in one of relatively stiff sections 2 of lead 10, as shown in FIG. 12C. Distalmost relatively stiff section 2 shown in FIG. 12C, like that shown in FIG. 12B, is most preferably about 5 mm to about 10 mm long.

FIG. 12C shows an embodiment of the present invention where more basal stimulation of patient's heart 1 is desired. Contrariwise, the embodiment of the present invention shown in FIG. 12D is configured such that electrodes 14(a) and 14(b) may be positioned deeper within a selected cardiac vein to permit more apical stimulation of heart 1.

Referring now to FIG. 12B, relatively stiff sections 2 are denoted by labels A, B, C, D and E. If basal ventricular pacing or defibrillation of heart 1 is desired, then it is preferred that the cathode electrode be positioned on or near section C or section B, and that the anode be positioned on or near section A or B. Alternatively, the cathode and anode may both be positioned on section C or section B of lead 10 to permit basal ventricular pacing.

In the event apical ventricular pacing is desired, the anode is most preferably located on section A or section B and the cathode is most preferably located on section B or section A, such that the anode is located on a section different from that of the cathode. Alternatively, and assuming apical ventricular pacing or defibrillation is desired, the anode and cathode may both be placed together on section A or section B of lead 10.

The anode and cathode may also be formed along or in a single relatively stiff section A, B, C, D or E when small inter-electrode distances are desired. Preferred anode to cathode inter-electrodes distance for pacing in the present invention range between about 4 mm and about 12 mm, with about a 5 mm inter-electrode distance being preferred.

The present invention may also be practiced as stated above in conjunction with an implantable defibrillator or the like. Defibrillation electrodes are most preferably employed as coiled electrodes, where coiled electrodes form at least a portion of relatively stiff section A of FIG. 12B. The preferred length of such an electrode or relatively stiff section is about 50 mm. Defibrillation electrodes may assume the shape of ring electrodes which coincide with relatively stiff sections 2 and be separated by relatively flexible sections 4.

Figure 13:
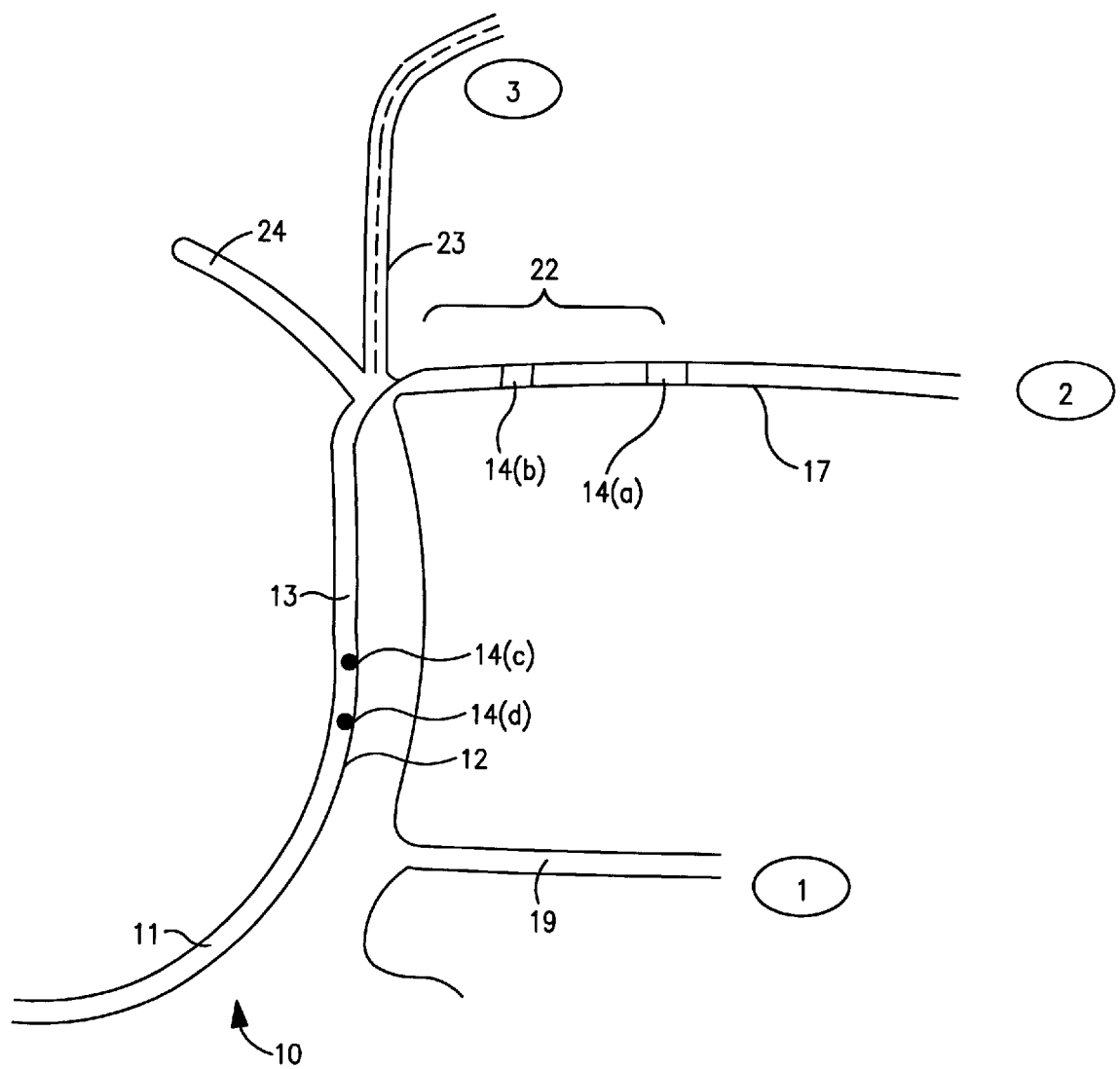
FIG. 13 illustrates a single pass dual chamber embodiment of a lead of the present invention.

FIG. 13 shows one embodiment of the present invention comprising single pass dual chamber lead 10. The distal portion of lead 10 extends into Posterior cardiac vein 17. Proximal from electrodes 14(a) and 14(b) of distal portion 22 of lead 10 are located electrodes 14(c) and 14(d) positioned in Coronary sinus 13. Electrodes 14(c) and 14(d) are positioned to stimulate the left atrium, while electrodes 14(a) and 14(b) are positioned to stimulate the left ventricle. The preferred distance between electrodes 14(c) and 14(d) ranges between about 20 mm and about 50 mm, but may be as large as about 60 mm or as little as about 15 mm. Lead 10 may also be implanted in great cardiac vein 23 such that distal electrodes 14(b) and 14(a) stimulate the left ventricle therefrom. Placement within posterior cardiac vein 17 of lead 10 shown in FIG. 13 permits apical pacing of the left ventricle to be accomplished whereas positioning of lead 10 in great cardiac vein 23 permits basal pacing of the left ventricle.

Figure 14:
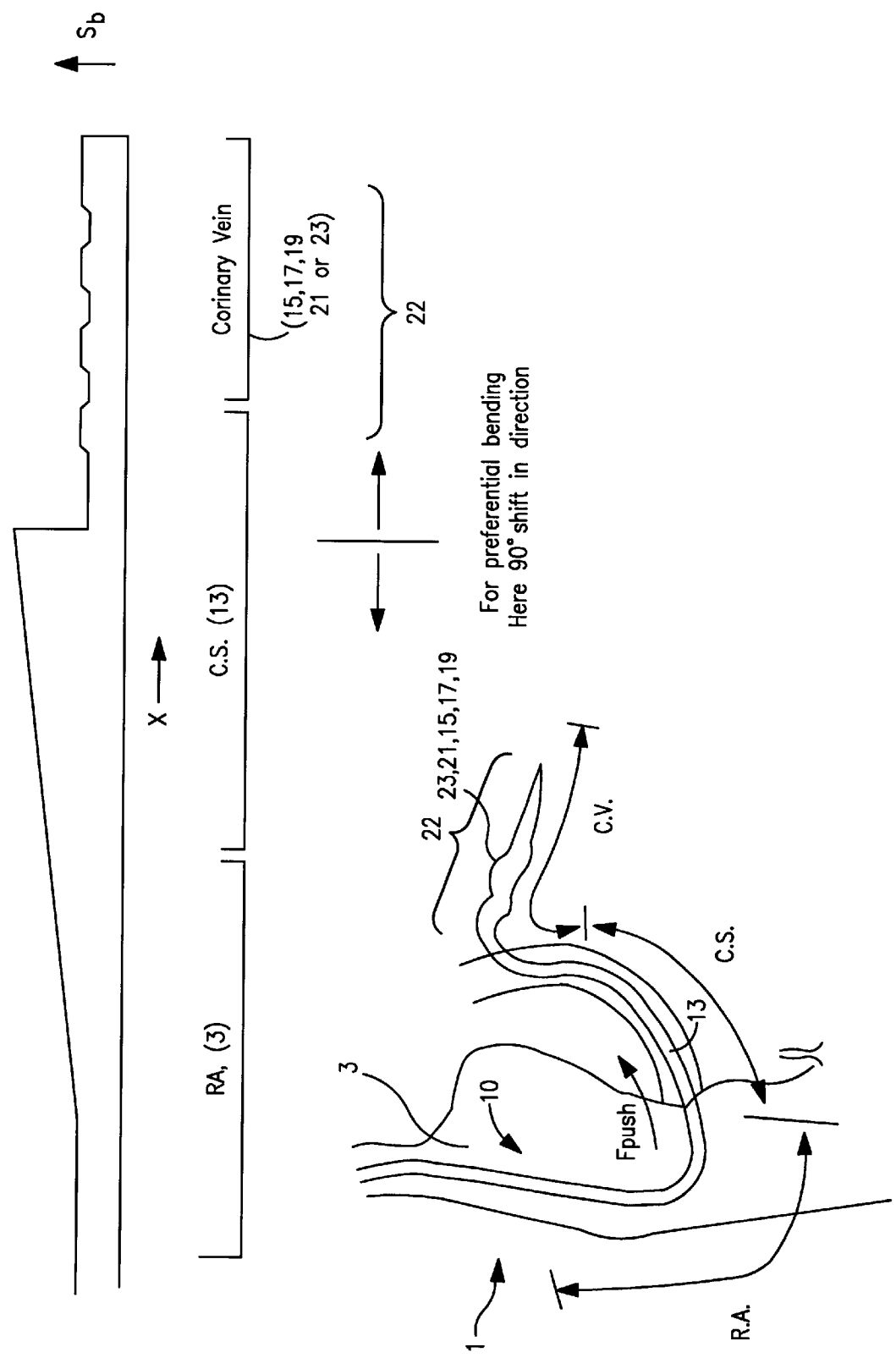
FIG. 14 illustrates another embodiment of the present invention, where a lead is adapted for implantation within various portions of the venous anatomy.

FIG. 14 illustrates another embodiment of the present invention, where lead 10 is adapted for implantation within right atrium 3, coronary sinus 13 and a selected cardiac vein. The distal tip 50 of lead 10 is disposed in the selected cardiac vein, while proximal therefrom a portion of lead 10 having bending stiffness characteristics which differ from those of the distalmost portions of lead 10. More particularly, and referring now to FIG. 14 again, it will be seen that distal portion 22 of lead 10 is characterized in having a bending stiffness profile which alternates between relatively stiff portions 2 and relatively flexible portions 4. Proximal from such sections of alternating relatively stiff and relatively flexible sections 2 and 4 there is disposed a section of lead body 12 in which bending stiffness increases in the distal direction, most preferably in the manner shown in FIG. 14. Note, however, that the increase in bending stiffness shown over those portions of lead 10 illustrated in FIG. 14 intended for implantation in right atrium 3, and optionally at least portions of coronary sinus 13, may increase monotonically, exponentially, step-wise or logrithmically. The important point is that bending stiffness over the portion of the lead implanted within the right atrium and optionally at least portions of the Coronary sinus have an increasing bending stiffness to create a force which will have a tendency to push the lead in the distal direction, even after implantation.

An outer layer or sleeve may surround lead body 12. Without any limitation intended, the sleeve may be constructed from a carbon coated silicone, steroid, steroid eluting silicone, or a combination of silicone and an antifibrotic surface treatment element. Any of those compositions may help reduce tissue response to lead insertion so that lead 10 will not cause clots or adhere to the vessel wall, thereby allowing retraction of the lead in the future, if necessary. These compositions may also help prevent encapsulation of the electrode, thereby enhancing the effectiveness of the pacing and sensing capabilities. These compositions may also be slippery to reduce friction between the lead and venous wall.

One or more electrical conductors are disposed on or in lead body 12 and convey signals sensed by electrode 14 or permit the delivery of electrical pacing or defibrillation signals therethrough. Such conductors may be helically wound coils or multistrand twisted cables, ETFE coated, or fixed within a longitudinally disposed lumen of the lead body 12. The distal end of lead conductor 16 may be attached to electrode 14 while the proximal end thereof is attached to terminal pin 18 by crimping or laser weld means well known to those skilled in the art. Without any limitation intended, electrode 14 and terminal pin 18 may be manufactured from titanium or platinum-plated titanium. Conductor 16 preferably comprises electrically conductive braided or stranded wires. A lumen 30 may be formed within lead body 12 wherein a stylet of known construction may be positioned therein.

Figure 15:
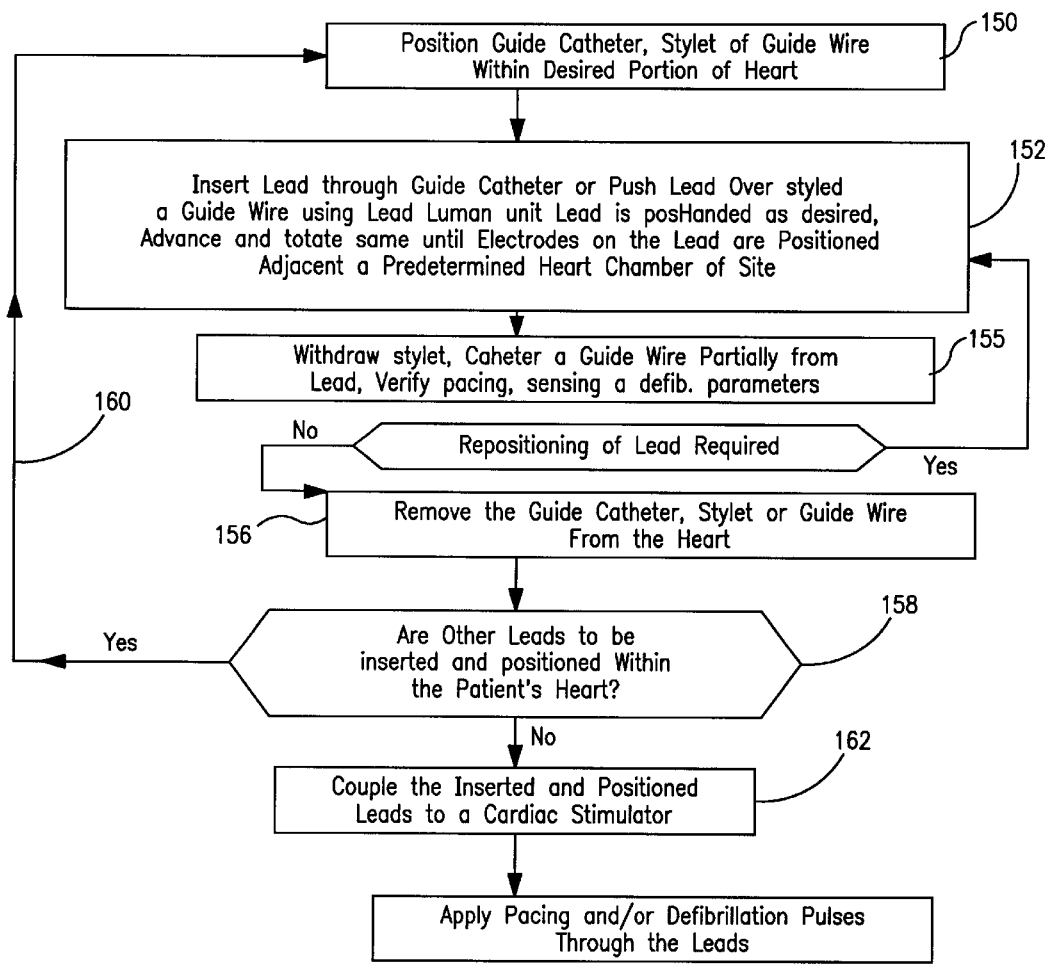
FIG. 15 illustrates several methods of implanting a lead of the present invention within a human heart and electrically stimulating same.

Having generally explained the features and positioning of lead 10, and referring now to the flow diagram of FIG. 15, some methods of pacing and/or defibrillating a patient's heart using a coronary vein lead 10 and implanting same will now be discussed. The method of pacing a patient's heart identified in the flow chart of FIG. 15 allows a user to effectively pace the left ventricle without increased risk of an ischemic episode.

The operator first positions a guide catheter of the tear away type known to those skilled in the art within coronary sinus 13 (block 150). Although the use of a guide catheter is not absolutely necessary, a guide catheter increases the ability of the operator to properly position lead 10 within a preselected coronary vein. Once the guide catheter has been positioned within coronary sinus 13, lead 10 is inserted through the lumen of the guide catheter and into a predetermined coronary vein under fluoroscopic observation (see Block 152). Lead 10 is positioned within the selected coronary vein, wherein the electrodes of lead 10 are aligned with the selected chambers to be paced. Those skilled in the art will appreciate that the electrodes may be constructed from a radiopaque material such that the position of the electrode is readily determined. After lead 10 is appropriately positioned in heart 1, the stylet or guide wire (if present) is removed from lead 10 (see block 154). The catheter is then removed from coronary sinus 13 (block 156) and the catheter is torn away as the catheter is pulled past the terminal pins of lead 10. Before removing the catheter from lead, however, electrical measurements may be taken. As noted above, a guide catheter may be used to direct a guide wire which is used to guide a support catheter to a desired position within a pre-selected coronary vein. The support catheter is then used to position lead 10 as described above.

After the guide catheter has been removed, the operator decides whether there are additional coronary vein leads to be inserted and positioned within the coronary veins of a patient's heart (see decision block 158). If other leads 10 are to be positioned within pre-selected coronary veins, then the above steps represented by blocks 150–156 are repeated (see loop 160). Those skilled in the art will appreciate that an additional lead of suitable construction could be positioned within the right ventricle. If no other leads 10 are to be inserted and positioned, then terminal pins 18 attached to each coronary vein lead 10 are coupled to corresponding terminal ports of cardiac stimulator 30 (block 162). Stimulator 30 is then programmed by known means to transmit a pacing and/or defibrillation pulse through each coupled lead 10 (block 164) to pace or defibrillate the pre-selected chamber of the patient's heart.

Once lead 10 of a suitable embodiment of the present invention has been inserted and positioned in heart 1, and without any limitation intended, the operator has the ability to, for example, pace or sense both the left atrium and left ventricle, or pace or sense the left atrium, left ventricle, and right atrium. When a separate right ventricular lead is positioned, pacing and/or sensing from all chambers of the heart may be possible. The diameter and construction of lead 10 provides the flexibility necessary to reduce substantially the likelihood that flexure of lead 10 will result in the coronary vein being eroded through. In this regard, the lead body 12 of lead 10 may be coated or impregnated with a biomedical steroid to reduce the inflammatory response of the coronary veins to the insertion and positioning of lead 10 therein. The selected biomedical steroid may also be used to reduce the amount of fiber build-up occurring between lead 10 and the coronary vein. Lead 10 may also be constructed to include an anchoring member such that lead 10 may be additionally anchored within the coronary vein or Coronary sinus.

Although specific embodiments of the invention have been set forth herein in some detail, it is to be understood that this has been done for the purposes of illustration only, and is not to be taken as a limitation on the scope of the invention as defined in the appended claims. Thus, the present invention may be carried out by using equipment and devices other than those described specifically herein. Various modifications, both as to the equipment and operating procedures, may be accomplished without departing from the scope of the invention itself. It is to be understood that various alternatives, substitutions and modifications may be made to the embodiment describe herein without departing from the spirit and scope of the appended claims.

In the claims, means-plus-function clauses are intended to cover the structures described herein as performing the recited function and not only structural equivalents but also equivalent structures. Thus, although surgical glue and a screw may not be structurally similar in that surgical glue employs chemical bonds to fasten biocompatible components together, whereas a screw employs a helical surface, in the environment of fastening means, surgical glue and a screw are equivalent structures.

All patents cited hereinabove are hereby incorporated by reference into the specification hereof, each in its respective entirety.

I claim:

1. An elongated implantable medical electrical lead for electrically stimulating a human heart or sensing electrical signals originating therefrom, comprising:

(a) a lead body having proximal and distal sections;

(b) at least one electrode at a distal end of the distal section of the lead body;

(c) an electrical connector at a proximal end of the lead body; and (d) at least one electrical conductor connected between the electrode and the electrical connector;

wherein the distal section of the lead body comprises at least first and second adjoining segments, the first segment being relatively stiff, the second segment being relatively flexible, the first and second segments being configured and dimensioned to assume a minimum stored mechanical energy implantation position when the lead is implanted within the coronary venous anatomy of the heart such that additional mechanical energy from an external source must be exerted upon the lead body along an axial direction to move the lead axially from the minimum stored mechanical energy implantation position, wherein the lead body comprises a first asymmetric cross-section configured for implantation in a first preferred orientation in pre-determined distal-most portions of the heart's venous anatomy where bending radii are small, a second asymmetric cross-section configured for implantation in a second preferred orientation different from the first orientation in pre-determined portions of the heart's venous anatomy located proximal from the distal-most portions thereof, wherein each of the first and second asymmetric cross-section lead body configurations is defined with respect to orthogonal cross-sectional bending axes and exhibits unequal bending stiffnesses around each axis of bending so as to produce asymmetric bending moments as a function of angular bending direction.

2. The elongated implantable medical electrical lead of claim 1 wherein each of said first and second asymmetric cross-section lead body configurations are selected from the group consisting of a flattened cross-section, a depression cross-section, a thickened cross-section and a thinned cross-section.

3. The elongated implantable medical electrical lead of claim 1 wherein the bending stiffness of said first cross-section is at least twice that of said second cross-section.

4. The elongated implantable medical electrical lead of claim wherein the bending stiffness of the distal section includes one of and combinations of incremental structural forms of step-wise, monotonic, exponential and logarithmic.

* * * * *

UNITED STATES PATENT AND TRADEMARK OFFICE
CERTIFICATE OF CORRECTION

PATENT NO.   : 6,741,893 B2
DATED        : May 25, 2004
INVENTOR(S)  : Karel F.A. Smits It is certified that error appears in the above-identified patent and that said Letters Patent is hereby corrected as shown below:

Column 20,
Line 33, after "claim" please insert -- 3 --.

Signed and Sealed this

Ninth Day of November, 2004

JON W. DUDAS
*Director of the United States Patent and Trademark Office*